US012590328B2

(12) United States Patent
Dannebaum et al.

(10) Patent No.: US 12,590,328 B2
(45) Date of Patent: Mar. 31, 2026

(54) TARGETED DEPLETION OF NON-TARGET LIBRARY MOLECULES USING POISON PRIMERS DURING TARGET CAPTURE OF NEXT-GENERATION SEQUENCING LIBRARIES

(71) Applicants:Roche Sequencing Solutions, Inc., Pleasanton, CA (US); Kapa Biosystems, Inc., Wilmington, MA (US)

(72) Inventors: Richard Dannebaum, Pleasant Hill, CA (US); Brian Christopher Godwin, Livermore, CA (US); David L. Penkler, Fish Hoek (ZA); Etienne Slabbert, Stellenbosch (ZA); Ruben van der Merwe, Pleasanton, CA (US)

(73) Assignees: ROCHE SEQUENCING SOLUTIONS, INC., Pleasanton, CA (US); KAPA BIOSYSTEMS, INC., Wilmington, MA (US)

( * ) Notice: Subject to any disclaimer, the term of this patent is extended or adjusted under 35 U.S.C. 154(b) by 605 days.

(21) Appl. No.: 18/004,365

(22) PCT Filed: Jul. 7, 2021

(86) PCT No.: PCT/EP2021/068782
§ 371 (c)(1),
(2) Date: Jan. 5, 2023

(87) PCT Pub. No.: WO2022/008578
PCT Pub. Date: Jan. 13, 2022

(65) Prior Publication Data
US 2024/0279725 A1     Aug. 22, 2024

Related U.S. Application Data

(60) Provisional application No. 63/049,255, filed on Jul. 8, 2020.

(51) Int. Cl.
| | | |
|---|---|---|
| *C12Q 1/68* | (2018.01) | |
| *C12Q 1/6848* | (2018.01) | |
| *C12Q 1/6876* | (2018.01) | |

(52) U.S. Cl.
CPC ......... *C12Q 1/6848* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 2018/0057855 A1* | 3/2018 | Englert | ................. C12Q 1/686 |
| 2019/0078148 A1 | 3/2019 | Zheng | |

FOREIGN PATENT DOCUMENTS

| | | |
|---|---|---|
| JP | 2008-161165 A | 7/2008 |
| JP | 2011-87534 A | 5/2011 |

(Continued)

OTHER PUBLICATIONS

Mark Edgley, et al., "Improved detection of small deletions in complex pools of DNA," Nucleic Acids Research 30(12):e52—(2002).

(Continued)

*Primary Examiner* — Aaron A Priest
(74) *Attorney, Agent, or Firm* — Eric Grant Lee

(57) ABSTRACT

The present disclosure is directed to compositions, kits, and methods of target enrichment by unidirectional primer extension, whereby the compositions, kits, and methods utilize both poison primers and target capture primers.

21 Claims, 14 Drawing Sheets

Specification includes a Sequence Listing.

(56) References Cited

FOREIGN PATENT DOCUMENTS

| | | | |
|---|---|---|---|
| JP | 2020-191833 A | 12/2020 | |
| WO | 2014/153408 A1 | 9/2014 | |
| WO | 2018/162538 A1 | 9/2018 | |
| WO | WO-2019121842 A1 * | 6/2019 | ........... C12Q 1/6813 |

OTHER PUBLICATIONS

Zhihai Ma, et al., "Profiling and Discovery of Novel miRNAs from Formalin-Fixed, Paraffin-Embedded Melanoma and Nodal Specimens," Journal of Molecular Diagnostics 11(5):420-429 (2009).

Timothy W. Nilsen, "Poisoned Primer Extension," Cold Spring Harbor Protocols 2015(1):132-134 (2015) (Cold Spring Harb Protoc; doi:10.1101/pdb.prot080986).

International Searching Authority, International Search Report for International Patent Application No. PCT/EP2021/068782 (Jan. 13, 2022).

International Searching Authority, Written Opinion of the International Searching Authority for International Patent Application No. PCT/EP2021/068782 (Jan. 13, 2022).

International Searching Authority, International Preliminary Report on Patentability for International Patent Application No. PCT/EP2021/068782 (Jan. 10, 2023).

* cited by examiner

TARGETED DEPLETION OF NON-TARGET LIBRARY MOLECULES USING POISON PRIMERS DURING TARGET CAPTURE OF NEXT-GENERATION SEQUENCING LIBRARIES

CROSS REFERENCE TO RELATED PATENT APPLICATIONS

This patent application is a U.S. national stage patent application of International Patent Application No. PCT/EP2021/068782, filed Jul. 7, 2021, which claims priority from U.S. Provisional Patent Application No. U.S. 63/049,255, filed Jul. 8, 2020, both of which are incorporated herein by reference in their entireties.

SEQUENCE LISTING

The instant patent application contains a Sequence Listing, which is hereby incorporated by reference in its entirety. The CRF copy, created Apr. 22, 2021, is named "35925-WO-SL," and is 21,000 bytes in size.

BACKGROUND OF THE DISCLOSURE

For many nucleic acid enrichment technologies, it can be useful to first provide a "shotgun library" of nucleic acid molecules, whereby longer nucleic acids sequences derived from a sample are subdivided into smaller fragments that are compatible with short read sequencing technologies (i.e., about 50-500 nucleotides). To prepare a shotgun library, a high-molecular-weight nucleic acid strand (typically cDNA or genomic DNA) is sheared into random fragments, optionally modified through ligation of common end sequences (i.e., adapters), and size-selected for downstream processing and analysis. For example, it may be useful to selectively capture a subset of the nucleic acids in the shotgun library.

Currently, there exist two general categories of capture technologies: hybridization-based capture and amplification-based capture. Hybridization-based capture methods offer the advantage of enabling recovery of the entirety of the original shotgun library fragment as opposed to replicating and recovering only a subset of the original library fragment. However, on-target rates associated with hybridization-based capture are generally lower in comparison with amplification-based methods. Notably, a lower on-target rate results in wasted sequencing capacity due to the necessity to sequence off-target capture product. Moreover, workflows associated with hybridization-based capture methods can be complex with long turnaround times relative to amplification-based approaches. By contrast, while amplification-based approaches such as anchored multiplex PCR methods offer the advantages of simple workflows, faster turnaround times and higher on-target rates relative to hybridization-based methods, there remain several disadvantages. For example, target capture primer sequences incorporated into library fragments following amplification result in wasted sequencing capacity. Moreover, library fragments are not necessarily representative of the original shotgun library as the template is necessarily truncated at the target specific primer binding site.

In some embodiments, shotgun target capture technology involves hybridization and extension of biotinylated primers. In some embodiments, this is followed by target enrichment using streptavidin bound magnetic beads. In some embodiments, the bound target library fragments can be released from the streptavidin using a non-biotinylated target release primer or directly amplified from the streptavidin beads (see, e.g., U.S. Patent Publication Nos. 2020/0032244 and 2018/0016630, the disclosures of which are hereby incorporated by reference herein in their entireties). In some embodiments, the target capture primers can, however, misprime, thus capturing and enriching unwanted library molecules, which may be amplified downstream and sequenced. It is believed that this may be problematic in cases where (i) the abundance of the unwanted molecules far exceeds that of the target molecules (e.g. high abundance of ribosomal RNA (rRNA) derived molecules in cDNA libraries since cDNA libraries typically include about 95% rRNA and about 5% mRNA derived molecules); and/or (ii) the low abundance of certain fusion transcripts as compared with wild-type transcripts makes detection challenging.

Depletion of undesired library molecules is a recurring theme when preparing and analyzing next-generation sequencing libraries. For instance, rRNA includes at least 90% of the total RNA extracted from mammalian tissue or cell line samples. Informative transcriptional profiling using massively parallel sequencing technologies requires either enrichment of mature poly-adenylated transcripts or targeted depletion of the rRNA fraction. Ribosomal depletion is a critical step in transcriptomics that allows for efficient detection of functionally relevant coding as well as non-coding transcripts through removal of highly abundant rRNA species. It is believed that ribosomal depletion, such as would occur prior to cDNA synthesis, is time-consuming and/or expensive.

BRIEF SUMMARY OF THE DISCLOSURE

It is desirable to reduce mis-priming events during the hybridization and extension steps of shotgun capture. It is also desirable to avoid the use of time consuming and costly rRNA depletion methods. In some embodiments, the present disclosure provides for a modified shotgun target capture approach whereby poison primers are included with target capture primers during any hybridization and extension steps. It is believed that the inclusion of poison primers which, as compared with the target capture primers, do not include a capture moiety, may prevent or reduce mispriming and off-target effects often observed during target enrichment. It is further believed that the presently disclosed methods of introducing poison primers in conjunction with target capture primers bypasses the need for a time-consuming rRNA removal method, e.g., ribosomal depletion, while still facilitating rRNA depletion during capture and enrichment steps. Additionally, it is believed that the presently disclosed methods may reduce the sequencing depth necessary to detect the desired target nucleic acid sequences.

In one aspect of the present disclosure is a method of enriching at least one target nucleic acid molecule in a library of nucleic acid molecules, the method comprising: hybridizing a first target capture primer to a first target nucleic acid molecule in the library of nucleic acid molecules, wherein the first target capture primer includes a capture moiety; hybridizing a first poison primer to a first non-target nucleic acid molecule in the library of nucleic acid molecules, wherein the first poison primer does not include any capture moiety; extending both the first hybridized target capture primer and the first hybridized poison primer, wherein the extension of the first hybridized target capture primer provides a first target capture primer extension complex comprising the first target nucleic acid molecule and the extended first target capture primer; and enriching the first target nucleic acid molecule relative to the library of nucleic acid molecules in the library of nucleic acid molecules. In some embodiments, the first target capture primer and the first poison primer are added as a pool of primers to the library. In some embodiments, each of the nucleic acid molecules in the library of nucleic acid molecules includes a first end including a first adapter and a second end including a second adapter. In some embodiments, the method does not include performing any ribosomal depletion steps.

In some embodiments, the extension of the first hybridized poison primer prevents or mitigates the first target capture primer from hybridizing to the first non-target nucleic acid molecule, i.e. the extension of the first hybridized poison primer prevents or mitigates mis-priming. In other embodiments, the extension of the first hybridized poison primer displaces a first target primer hybridized to the first non-target nucleic acid molecule, i.e. the extension of the first hybridized poison primer displaces a first target primer which has mis-primed to the first non-target nucleic acid molecule.

In some embodiments, the method further includes amplifying the first target nucleic acid molecule with a first amplification primer and a second amplification primer, wherein the first amplification primer includes a 3' end complementary to the first adapter, and wherein the second amplification primer includes a 3' end complementary to the second adapter. In some embodiments, the method further includes sequencing the amplified target nucleic acid molecule.

In some embodiments, the enriching of the first target nucleic acid molecule relative to the library of nucleic acid molecules includes (i) capturing the first target capture primer extension complex; (i) removing un-captured non-target nucleic acid molecules; and (ii) releasing the first target nucleic acid molecule from the captured first target capture primer extension complex. In some embodiments, the capturing of the first target capture primer extension complex includes contacting the first target capture primer extension complex with a functionalized substrate.

In some embodiments, the capture moiety of the first target capture primer includes a first member of a pair of specific binding entities, and wherein the functionalized substrate includes a second member of the pair of specific binding entities. In some embodiments, the first member of the pair of specific binding entities is selected from the group consisting of biotin, an antigenic molecule, an enzyme substrate, a receptor ligand, a polysaccharide, a thiolated molecule, and an amine-terminated molecule. In some embodiments, the second member of the pair of specific binding entities is selected from the group consisting of streptavidin, an antibody, an enzyme, a receptor, a lectin, a gold particle, and an NHS-activated moiety. In some embodiments, the capture moiety of the first target capture primer includes biotin. In some embodiments, the functionalized surfaced includes streptavidin. In some embodiments, the functionalized substrate includes beads having a surface functionalized with a second member of the pair of specific binding entities. In some embodiments, the functionalized substrate includes beads having a surface including a plurality of streptavidin molecules.

In some embodiments, the first target capture primer is coupled to a substrate through the capture moiety prior to the hybridizing of the first target capture primer to the first target nucleic acid molecule in the library of nucleic acid molecules. In some embodiments, the hybridizing of the first target capture primer to the first target nucleic acid molecule and/or the extending of the first hybridized target capture primer thereby captures the first target nucleic acid molecule to the substrate.

In some embodiments, the capturing of the first target capture primer extension complex includes: (i) hybridizing a universal capture oligonucleotide to the capture moiety of the first target capture primer extension complex to form a universal capture oligonucleotide complex, wherein the universal capture oligonucleotide includes (a) a first member of a pair of specific binding entities, and (b) a nucleotide sequence complementary to at least a portion of a capture sequence of the capture moiety; (ii) contacting the universal capture complex with a functionalized substrate, wherein the functionalized substrate includes a send member of the pair of specific binding entities.

In some embodiments, the removing of the un-captured nucleic acid molecules includes washing away the un-captured non-target nucleic acid molecules. In some embodiments, the releasing of the captured first target capture primer extension complex includes: (i) hybridizing a release primer to the first target nucleic acid molecule; and (b) extending the hybridized release primer. In some embodiments, the hybridized first target capture primer is extended with a first polymerase; and wherein the hybridized release primer is extended with a second polymerase. In some embodiments, the first and second polymerases are different. In some embodiments, the first target capture primer has a melting temperature which is greater than a melting temperature of the first poison primer.

In some embodiments, the library of nucleic acid molecules includes a plurality of target nucleic acid molecules and a plurality of non-target nucleic acid molecules, wherein the plurality of target nucleic acid molecules are in low abundance as compared with the plurality of non-target nucleic acid molecules. In some embodiments, the plurality of target nucleic acid molecules comprise less than about 10% of the nucleic acid molecules in the library of nucleic acid molecules. In some embodiments, the plurality of target nucleic acid molecules comprise less than about 5% of the nucleic acid molecules in the library of nucleic acid molecules. In some embodiments, the plurality of target nucleic acid molecules include mRNA-derived nucleic acid molecules. In some embodiments, the plurality of target nucleic acid molecules include fusion transcripts.

In another aspect of the present disclosure is a kit comprising: a first target capture primer, the first target capture primer being complementary to a target nucleic acid molecule in a library of nucleic acid molecules, and wherein the first target capture primer includes a capture moiety; and a first poison primer, the first poison primer being complementary to a non-target nucleic acid molecule in the library of nucleic acid molecules, and wherein the first poison primer does not include a capture moiety. In some embodiments, the first target capture primer has a Tm ranging from between about 55° C. to about 65° C. In some embodiments, the first poison primer has a Tm ranging from between about 65° C. to about 68° C. In some embodiments, the kit further includes at least one polymerase. In some embodiments, the kit further includes at least two different polymerases. In some embodiments, the kit further includes a plurality of nucleotides. In some embodiments, the kit further includes one or more buffer solutions and/or wash solutions. In some embodiments, the kit further includes beads having a functionalized surface. In some embodiments, the kit further includes one or more release primers. In some embodiments, the kit further comprises first and second amplification primers.

In another aspect of the present disclosure is a composition comprising: a nucleic acid molecule library, wherein the nucleic acid molecule library includes a plurality of target nucleic acid molecules and a plurality of non-target nucleic acid molecules, wherein the plurality target nucleic acid molecules are in low abundance as compared with the plurality of non-target nucleic acid molecules; a first target capture primer, the first target capture primer being complementary to a first target nucleic acid molecule in the library of nucleic acid molecules, and wherein the first target capture primer includes a capture moiety; a first poison primer, the first poison primer being complementary to a first non-target nucleic acid molecule in the library of nucleic acid molecules, and wherein the first poison primer does not include a capture moiety; and a first polymerase. In some embodiments, the composition further includes a second polymerase which differs from the first polymerase. In some embodiments, the composition further includes a functionalized substrate. In some embodiments, the composition further includes one or more adapter molecules. In some embodiments, the composition further includes one or more release primers. In some embodiments, the composition further includes first and second amplification primers.

In another aspect of the present disclosure is a composition comprising: a nucleic acid molecule library, wherein the nucleic acid molecule library includes a plurality of target nucleic acid molecules and a plurality of non-target nucleic acid molecules; a first target capture primer hybridized to a portion of a first target nucleic acid molecule in the library of nucleic acid molecules, and wherein the first target capture primer includes a capture moiety which is bound to a functionalized substrate; a first poison primer hybridized to a portion of a first non-target nucleic acid molecule in the library of nucleic acid molecules, and wherein the first poison primer does not include a capture moiety. In some embodiments, the plurality of target nucleic acid molecules are in low abundance as compared with the plurality of non-target nucleic acid molecules.

In some embodiments, the capture moiety includes a first member of the pair of specific binding entities. In some embodiments, the functionalized substrate is a bead having a surface functionalized with a second member of a pair of specific binding entities. In some embodiments, the first member of the pair of specific binding entities is selected from the group consisting of biotin, an antigenic molecule, an enzyme substrate, a receptor ligand, a polysaccharide, a thiolated molecule, and an amine-terminated molecule. In some embodiments, the second member of the pair of specific binding entities is selected from the group consisting of streptavidin, an antibody, an enzyme, a receptor, a lectin, a gold particle, and an NHS-activated moiety. In some embodiments, the capture moiety of the first target capture primer includes biotin. In some embodiments, the functionalized surfaced includes streptavidin.

In another aspect of the present disclosure is a composition enriched in target nucleic acid molecules, the composition prepared by: (i) hybridizing a first target capture primer to a first target nucleic acid molecule in a library of nucleic acid molecules, wherein the library of nucleic acid molecules includes a plurality of target nucleic acid molecules and a plurality of non-target nucleic acid molecules, wherein the plurality of target nucleic acid molecules are in low abundance as compared with the plurality of non-target nucleic acid molecules, and wherein the first target capture primer includes a capture moiety; (ii) hybridizing a first poison primer to a first non-target nucleic acid molecule in the library of nucleic acid molecules, wherein the first poison primer does not include any capture moiety; (iii) extending both the first hybridized target capture primer and the first hybridized poison primer, wherein the extension of the first hybridized target capture primer provides a first target capture primer extension complex comprising the first target nucleic acid molecule and the extended first target capture primer; and (iv) enriching the first target nucleic acid molecule relative to the library of nucleic acid molecules in the library of nucleic acid molecules.

In some embodiments, the composition is enriched with low abundance fusion transcripts. In some embodiments, the composition is enriched with mRNA-derived molecules. In some embodiments, the composition enriched in target nucleic acid molecules is prepared without performing any ribosomal depletion steps.

In some embodiments, the first target capture primer and the first poison primer are added as a pool of primers to the library. In some embodiments, each of the nucleic acid molecules in the library of nucleic acid molecules includes a first end including a first adapter and a second end including a second adapter.

In some embodiments, the method further includes amplifying the first target nucleic acid molecule with a first amplification primer and a second amplification primer, wherein the first amplification primer includes a 3' end complementary to the first adapter, and wherein the second amplification primer includes a 3' end complementary to the second adapter. In some embodiments, the method further includes sequencing the amplified target nucleic acid molecule.

In some embodiments, the enriching of the first target nucleic acid molecule relative to the library of nucleic acid molecules includes (i) capturing the first target capture primer extension complex; (i) removing un-captured non-target nucleic acid molecules; and (ii) releasing the first target nucleic acid molecule from the captured first target capture primer extension complex. In some embodiments, the capturing of the first target capture primer extension complex includes contacting the first target capture primer extension complex with a functionalized substrate.

In some embodiments, the capture moiety of the first target capture primer includes a first member of a pair of specific binding entities, and wherein the functionalized substrate includes a second member of the pair of specific binding entities. In some embodiments, the first member of the pair of specific binding entities is selected from the group consisting of biotin, an antigenic molecule, an enzyme substrate, a receptor ligand, a polysaccharide, a thiolated molecule, and an amine-terminated molecule. In some embodiments, the second member of the pair of specific binding entities is selected from the group consisting of streptavidin, an antibody, an enzyme, a receptor, a lectin, a gold p article, and an NHS-activated moiety. In some embodiments, the capture moiety of the first target capture primer includes biotin. In some embodiments, the functionalized surfaced includes streptavidin. In some embodiments, the functionalized substrate includes beads having a surface functionalized with a second member of the pair of specific binding entities. In some embodiments, the functionalized substrate includes beads having a surface including a plurality of streptavidin molecules.

In some embodiments, the first target capture primer is coupled to a substrate through the capture moiety prior to the hybridizing of the first target capture primer to the first target nucleic acid molecule in the library of nucleic acid molecules. In some embodiments, the hybridizing of the first target capture primer to the first target nucleic acid molecule and/or the extending of the first hybridized target capture primer thereby captures the first target nucleic acid molecule to the substrate.

In some embodiments, the capturing of the first target capture primer extension complex includes: (i) hybridizing a universal capture oligonucleotide to the capture moiety of the first target capture primer extension complex to form a universal capture oligonucleotide complex, wherein the universal capture oligonucleotide includes (a) a first member of a pair of specific binding entities, and (b) a nucleotide sequence complementary to at least a portion of a capture sequence of the capture moiety; (ii) contacting the universal capture complex with a functionalized substrate, wherein the functionalized substrate includes a second member of the pair of specific binding entities.

In some embodiments, the removing of the un-captured nucleic acid molecules includes washing away the un-captured non-target nucleic acid molecules. In some embodiments, the releasing of the captured first target capture primer extension complex includes: (i) hybridizing a release primer to the first target nucleic acid molecule; and (b) extending the hybridized release primer. In some embodiments, the hybridized first target capture primer is extended with a first polymerase; and wherein the hybridized release primer is extended with a second polymerase.

BRIEF DESCRIPTION OF THE FIGURES

For a general understanding of the features of the disclosure, reference is made to the drawings. In the drawings, like reference numerals have been used throughout to identify identical elements.

FIG. 6 further illustrates that a target capture primer coupled to a substrate through a capture moiety may be mis-primed to a non-target nucleic acid molecule, and where the capture moiety coupled to the substrate may be liberated through the extension of a hybridized poison primer.

DETAILED DESCRIPTION

Figure 1A:
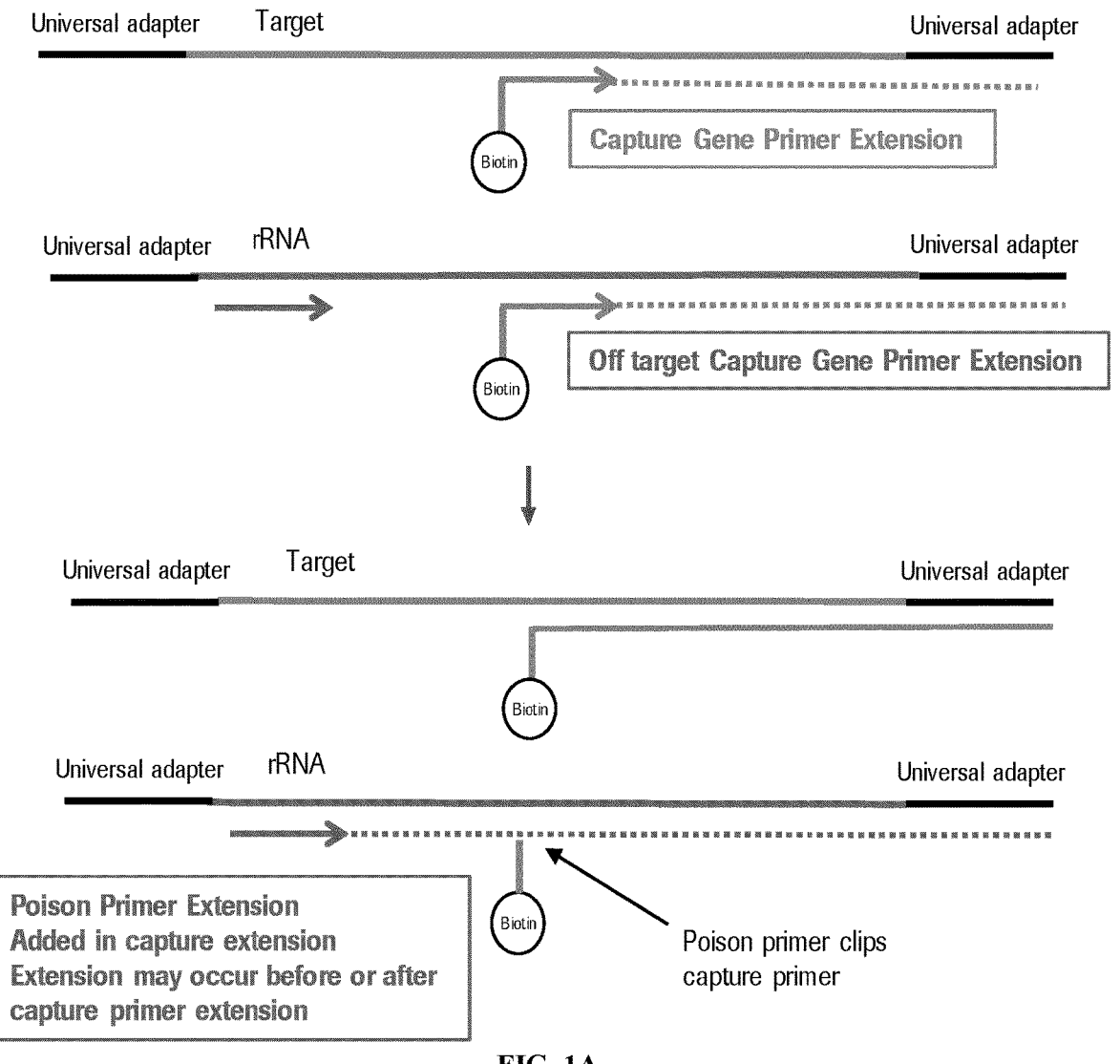
FIG. 1A provides an overview of the use of poison primers in conjunction with target capture primers to effectuate the targeted depletion of non-target nucleic acid molecules from a nucleic acid library. In some embodiments, the non-target nucleic acid molecules are rRNA-derived cDNA molecules.

It should also be understood that, unless clearly indicated to the contrary, in any methods claimed herein that include more than one step or act, the order of the steps or acts of the method is not necessarily limited to the order in which the steps or acts of the method are recited.

Definitions

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b, and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the term "adapter" refers a nucleotide sequence that may be added to another sequence so as to import additional properties to that sequence. An adapter can be single- or double-stranded, or may have both a single-stranded portion and a double-stranded portion.

As used herein "amplification" refers to a process in which a copy number increases. Amplification may be a process in which replication occurs repeatedly over time to form multiple copies of a template. Amplification can produce an exponential or linear increase in the number of copies as amplification proceeds. Exemplary amplification strategies include polymerase chain reaction (PCR), loop-mediated isothermal amplification (LAMP), rolling circle replication (RCA), cascade-RCA, nucleic acid based amplification (NASBA), and the like. Also, amplification can utilize a linear or circular template. Amplification can be performed under any suitable temperature conditions, such as with thermal cycling or isothermally. Furthermore, amplification can be performed in an amplification mixture (or reagent mixture), which is any composition capable of amplifying a nucleic acid target, if any, in the mixture. PCR amplification relies on repeated cycles of heating and cooling (i.e., thermal cycling) to achieve successive rounds of replication. PCR can be performed by thermal cycling between two or more temperature setpoints, such as a higher denaturation temperature and a lower annealing/extension temperature, or among three or more temperature setpoints, such as a higher denaturation temperature, a lower annealing temperature, and an intermediate extension temperature, among others. PCR can be performed with a thermostable polymerase, such as Taq DNA polymerase. PCR generally produces an exponential increase in the amount of a product amplicon over successive cycles.

As used herein, the term "complementary" generally refers to the capability for precise pairing between two nucleotides. The term "complementary" refers to the ability to form favorable thermodynamic stability and specific pairing between the bases of two nucleotides at an appropriate temperature and ionic buffer conditions. Complementarity is achieved by distinct interactions between the nucleobases adenine, thymine (uracil in RNA), guanine and cytosine, where adenine pairs with thymine or uracil, and guanine pairs with cytosine. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence.

As used herein, the terms "complementary DNA" or "cDNA" refer to DNA which is copied from RNA. In some embodiments, cDNA is the DNA produced on an RNA template by the action of reverse transcriptase (RNA-dependent DNA-polymerase. cDNA copied from mRNA does not include the various non-coding sequences characteristic of genomic DNA.

As used herein, the term "cDNA library" as used herein refers to a collection of cDNAs representing the messenger RNAs expressed in a cell or tissue type.

As used herein, the term "conjugate" refers to two or more molecules (and/or materials such as nanoparticles) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules, such as one or more other biomolecules.

As used herein, the term "enrichment" refers to the process of increasing the relative abundance of a population of molecules, e.g. nucleic acid molecules, in a sample relative to the total amount of the molecules initially present in the sample before treatment. Thus, an enrichment step provides a percentage or fractional increase rather than directly increasing for example, the copy number of the nucleic acid sequences of interest as amplification methods, such as a polymerase chain reaction, would.

As used herein, the term "fluid" refers to any liquid or liquid composition, including water, solvents, buffers, solutions (e.g. polar solvents, non-polar solvents), washes or washing solutions, and/or mixtures. The fluid may be aqueous or non-aqueous. In some embodiments, washing solutions include a surfactant to facilitate spreading of the washing liquids over the specimen-bearing surfaces of the slides. In some embodiments, acid solutions include deionized water, an acid (e.g., acetic acid), and a solvent. In some embodiments, alkaline solutions include deionized water, a base, and a solvent. In some embodiments, transfer solutions include one or more glycol ethers, such as one or more propylene-based glycol ethers (e.g., propylene glycol ethers, di(propylene glycol) ethers, and tri(propylene glycol) ethers, ethylene-based glycol ethers (e.g., ethylene glycol ethers, di(ethylene glycol) ethers, and tri(ethylene glycol) ethers), and functional analogs thereof.

Non-liming examples of buffers include citric acid, potassium dihydrogen phosphate, boric acid, diethyl barbituric acid, piperazine-N,N'-bis(2-ethanesulfonic acid), dimethylarsinic acid, 2-(N-morpholino)ethanesulfonic acid, tris(hydroxymethyl)methylamine (TRIS), 2-(N-morpholino)ethanesulfonic acid (TAPS), N,N-bis(2-hydroxyethyl)glycine (Bicine), N-tris(hydroxymethyl)methylglycine (Tricine), 4-2-hydroxyethyl-1-piperazineethanesulfonic acid (HEPES), 2-{[tris(hydroxymethyl)methyl] amino}ethanesulfonic acid (TES), and combinations thereof. In other embodiments, the buffer may be comprised of tris(hydroxymethyl)methylamine (TRIS), 2-(N-morpholino)ethanesulfonic acid (TAPS), N,N-bis(2-hydroxyethyl)glycine (Bicine), N-tris(hydroxymethyl)methylglycine (Tricine), 4-2-hydroxyethyl-1-piperazineethanesulfonic acid (HEPES), 2-{[tris(hydroxymethyl)methyl] amino}ethanesulfonic acid (TES), or a combination thereof. Additional wash solutions, transfer solutions, acid solutions, and alkaline solutions are described in United States Patent Application Publication No. 2016/0282374, the disclosure of which is hereby incorporated by reference herein in its entirety.

As used herein, the term "hybridize" refers to the base-pairing between different nucleic acid molecules consistent with their nucleotide sequences.

As used herein, the phrase "next generation sequencing (NGS)" refers to sequencing technologies having high-throughput sequencing as compared to traditional Sanger- and capillary electrophoresis-based approaches, wherein the sequencing process is performed in parallel, for example producing thousands or millions of relatively small sequence reads at a time. Some examples of next generation sequencing techniques include, but are not limited to, sequencing by synthesis, sequencing by ligation, and sequencing by hybridization. These technologies produce shorter reads (anywhere from about 25 to about 500 bp) but many hundreds of thousands or millions of reads in a relatively short time. The term "next-generation sequencing" refers to the so-called parallelized sequencing-by-synthesis or sequencing-by-ligation platforms currently employed by Illumina, Life Technologies, and Helicos Biosciences. Next-generation sequencing methods may also include nanopore sequencing methods with electronic-detection (Oxford Nanopore and Roche Diagnostics).

As used herein, the terms "nucleic acid" or "polynucleotide" (used interchangeably herein) refer to a polymeric form of nucleotides of any length, either deoxyribonucleotides or ribonucleotides, or analogs thereof. Polynucleotides may have any three-dimensional structure, and may perform any function, known or unknown. Unless specifically limited, the terms encompass nucleic acids or polynucleotides including known analogues of natural nucleotides that have similar binding properties as the reference nucleic acid and are metabolized in a manner similar to naturally occurring nucleotides. Non-limiting examples of polynucleotides include coding or non-coding regions of a gene or gene fragment, loci (locus) defined from linkage analysis, exons, introns, messenger RNA (mRNA), transfer RNA, ribosomal RNA, ribozymes, cDNA, synthetic polynucleotides, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. Unless otherwise indicated, a particular nucleic acid sequence also implicitly encompasses conservatively modified variants thereof (e.g., degenerate codon substitutions), alleles, orthologues, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

As used herein, the term "oligonucleotide," refers to an oligomer of nucleotide or nucleoside monomer units wherein the oligomer optionally includes non-nucleotide monomer units, and/or other chemical groups attached at internal and/or external positions of the oligomer. The oligomer can be natural or synthetic and can include naturally-occurring oligonucleotides, or oligomers that include nucleosides with non-naturally-occurring (or modified) bases, sugar moieties, phosphodiester-analog linkages, and/or alternative monomer unit chiralities and isomeric structures (e.g., 5'- to 2'-linkage, L-nucleosides, α-anomer nucleosides, (β-anomer nucleosides, locked nucleic acids (LNA), peptide nucleic acids (PNA)).

As used herein, a "reaction" between any two different reactive groups (such as any two reactive groups of a reagent and a particle) may mean that a covalent linkage is formed between the two reactive groups (or two reactive functional groups); or may mean that the two reactive groups (or two reactive functional groups) associate with each other, interact with each other, hybridize to each other, hydrogen bond with each other, etc. In some embodiments, the "reaction" includes binding events, e.g., binding events between reactive function groups or binding events between first and second members of a pair of specific binding entities.

As used herein, the term "polymerase" refers to an enzyme that performs template-directed synthesis of polynucleotides. A DNA polymerase can add free nucleotides only to the 3' end of the newly forming strand. This results in elongation of the newly forming strand in a 5'-3' direction. No known DNA polymerase is able to begin a new chain (de novo). DNA polymerase can add a nucleotide only on to a pre-existing 3'-OH group, and, therefore, needs a primer at which it can add the first nucleotide. Non-limiting examples of polymerases include prokaryotic DNA polymerases (e.g., Pol I, Pol II, Pol III, Pol IV and Pol V), eukaryotic DNA polymerase, archaeal DNA polymerase, telomerase, reverse transcriptase and RNA polymerase. Reverse transcriptase is an RNA-dependent DNA polymerase which synthesizes DNA from an RNA template. The reverse transcriptase family contain both DNA polymerase functionality and RNase H functionality, which degrades RNA base-paired to DNA. RNA polymerase, is an enzyme that synthesizes RNA using DNA as a template during the process of gene transcription. RNA polymerase polymerizes ribonucleotides at the 3' end of an RNA transcript.

In some embodiments, a polymerase from the following may be used in a polymerase-mediated primer extension, end-modification (e.g., terminal transferase, degradation, or polishing), or amplification reaction: archaea (e.g., *Thermococcus litoralis* (Vent, GenBank: AAA72101), *Pyrococcus furiosus* (Pfu, GenBank: D12983, BAA02362), *Pyrococcus woesii, Pyrococcus* GB-D (Deep Vent, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulforococcus, Pyrolobus, Pyrodictium, Staphylothermus, Vulcanisaetta, Methanococcus* (GenBank: P52025) and other archaeal B polymerases, such as GenBank AAC62712, P956901, BAAA07579)), thermophilic bacteria *Thermus* species (e.g., *flavus, ruber, thermophilus, lacteus, rubens, aquaticus*), *Bacillus stearothermophilus, Thermotoga maritima, Methanothermus fervidus*, KOD polymerase, TNA1 polymerase, *Thermococcus* sp. 9 degrees N-7, T4, T7, phi29, *Pyrococcus furiosus, P. abyssi, T. gorgonarius, T. litoralis, T. zilligii*, T. sp. GT, P. sp. GB-D, KOD, Pfu, *T. gorgonarius, T. zilligii, T. litoralis* and *Thermococcus* sp. 9N-7 polymerases.

As used herein, the term "thermostable polymerase" refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in, e.g., U.S. Pat. Nos. 4,683,202, 4,683,195, and 4,965,188, which are incorporated herein by reference. As used herein, a thermostable polymerase is suitable for use in a temperature cycling reaction such as the polymerase chain reaction ("PCR"), a primer extension reaction, or an end-modification (e.g., terminal transferase, degradation, or polishing) reaction. Irreversible denaturation for purposes herein refers to permanent and complete loss of enzymatic activity. For a thermostable polymerase, enzymatic activity refers to the catalysis of the combination of the nucleotides in the proper manner to form polynucleotide extension products that are complementary to a template nucleic acid strand. Thermostable DNA polymerases from thermophilic bacteria include, e.g., DNA polymerases from *Thermotoga maritima, Thermus aquaticus, Thermus thermophilus, Thermus flavus, Thermus filiformis, Thermus* species sps17, *Thermus* species Z05, *Thermus caldophilus, Bacillus caldotenax, Thermotoga neopolitana, Thermosipho africanus*, and other thermostable DNA polymerases disclosed above.

In some cases, the nucleic acid (e.g., DNA or RNA) polymerase may be a modified naturally occurring Type A polymerase. A further embodiment of the invention generally relates to a method wherein a modified Type A polymerase, e.g., in a primer extension, end-modification (e.g., terminal transferase, degradation, or polishing), or amplification reaction, may be selected from any species of the genus *Meiothermus, Thermotoga*, or *Thermomicrobium*. Another embodiment of the invention generally pertains to a method wherein the polymerase, e.g., in a primer extension, end-modification (e.g., terminal transferase, degradation or polishing), or amplification reaction, may be isolated from any of *Thermus aquaticus* (Taq), *Thermus thermophilus, Thermus caldophilus*, or *Thermus filiformis*. A further embodiment of the invention generally encompasses a method wherein the modified Type A polymerase, e.g., in a primer extension, end-modification (e.g., terminal transferase, degradation, or polishing), or amplification reaction, may be isolated from *Bacillus stearothermophilus, Sphaerobacter thermophilus, Dictoglomus thermophilum*, or *Escherichia coli*. In another embodiment, the invention generally relates to a method wherein the modified Type A polymerase, e.g., in a primer extension, end-modification (e.g., terminal transferase, degradation, or polishing), or amplification reaction, may be a mutant Taq-E507K polymerase. Another embodiment of the invention generally pertains to a method wherein a thermostable polymerase may be used to effect amplification of the target nucleic acid.

As used herein, the term "primer" refers to an oligonucleotide which binds to a specific region of a single-stranded template nucleic acid molecule and initiates nucleic acid synthesis via a polymerase-mediated enzymatic reaction, extending from the 3' end of the primer and complementary to the sequence of the template molecule. PCR amplification primers can be referred to as 'forward' and 'reverse' primers, one of which is complementary to a nucleic acid strand and the other of which is complementary to the complement of that strand. Typically, a primer comprises fewer than about 100 nucleotides and preferably comprises fewer than about 30 nucleotides. Exemplary primers range from about 5 to about 25 nucleotides. Primers can comprise, for example, RNA and/or DNA bases, as well as non-naturally occurring bases. The directionality of the newly forming strand (the daughter strand) is opposite to the direction in which DNA polymerase moves along the template strand. In some cases, a target capture primer specifically hybridizes to a target polynucleotide under hybridization conditions. Such hybridization conditions can include, but are not limited to, hybridization in isothermal amplification buffer (20 mM Tris-HCl, 10 mM $(NH_4)_2SO_4$), 50 mM KCl, 2 mM $MgSO_4$, 0.1% TWEEN® 20, pH 8.8 at 25° C.) at a temperature of about 40° C., 45° C., 50° C., 55° C., 60° C., 65° C., or 70° C.

As used herein, the term "sequence," when used in reference to a nucleic acid molecule, refers to the order of nucleotides (or bases) in the nucleic acid molecules. In cases, where different species of nucleotides are present in the nucleic acid molecule, the sequence includes an identification of the species of nucleotide (or base) at respective positions in the nucleic acid molecule. A sequence is a property of all or part of a nucleic acid molecule. The term can be used similarly to describe the order and positional identity of monomeric units in other polymers such as amino acid monomeric units of protein polymers.

As used herein, the term "sequencing" refers to the determination of the order and position of bases in a nucleic acid molecule. More particularly, the term "sequencing" refers to biochemical methods for determining the order of the nucleotide bases, adenine, guanine, cytosine, and thymine, in a DNA oligonucleotide. Sequencing, as the term is used herein, can include without limitation parallel sequencing or any other sequencing method known of those skilled in the art, for example, chain-termination methods, rapid DNA sequencing methods, wandering-spot analysis, Maxam-Gilbert sequencing, dye-terminator sequencing, or using any other modern automated DNA sequencing instruments.

As used herein, the term "substrate" refers to any material capable of interacting with a capture moiety. In some embodiments, the substrate is a solid support. In some embodiments, a solid support may encompass any type of solid, porous, or hollow sphere, ball, bearing, cylinder, capillary, channel, or other similar configuration composed of plastic, ceramic, metal, or polymeric material (e.g., hydrogel) onto which a nucleic acid molecule may be immobilized (e.g., covalently or non-covalently). In some embodiments, a solid support may comprise a discrete particle that may be spherical (e.g., microspheres) or have a non-spherical or irregular shape, such as cubic, cuboid, pyramidal, cylindrical, conical, oblong, or disc-shaped, and the like. In some embodiments, a solid support may include silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms. In some embodiments, a solid support may be a solution-phase support capable of suspension in a solution (e.g., a glass bead, a magnetic bead, or another like particle), or a solid-phase support (e.g., a silicon wafer, a glass slide, or the like). Non-limiting examples of solution-phase supports include superparamagnetic spherical polymer particles such as DYNABEADS magnetic beads from INVITROGEN or magnetic glass particles such as described in U.S. Pat. Nos.

656,568, 6,274,386, 7,371,830, 6,870,047, 6,255,477, 6,746, 874 and 6,258,531, the disclosures of which are hereby incorporated by reference herein in their entireties.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Examples of specific binding moieties include specific binding proteins (for example, antibodies, lectins, avidins such as streptavidins, and protein A). Specific binding moieties can also include the molecules (or portions thereof) that are specifically bound by such specific binding proteins.

As used herein, the term "substantially" means the qualitative condition of exhibiting total or near-total extent or degree of a characteristic or property of interest. In some embodiments, "substantially" means within about 5%. In some embodiments, "substantially" means within about 10%. In some embodiments, "substantially" means within about 15%. In some embodiments, "substantially" means within about 20%.

As used herein, the terms "target" or "target sequence" refer to nucleic acid molecule sequences of interest, e.g., those which hybridize to oligonucleotide probes.

As used herein, the term "universal primer" refers to a primer that can hybridize to and support amplification of target polynucleotides having a shared complementary universal primer binding site. Similar, the term "universal primer pair" refers to a forward and reverse primer pair that can hybridize to and support PCR amplification of target polynucleotides having shared complementary forward and reverse universal primer binding sites. Such universal primer(s) and universal primer binding site(s) can allow single or double primer mediated universal amplification (e.g., universal PCR) of target polynucleotide regions of interest. The headings provided herein are for convenience only and do not interpret the scope or meaning of the disclosed embodiments.

Overview

The present disclosure is directed to compositions, kits, and methods of target enrichment by unidirectional primer extension, whereby the compositions, kits, and methods utilize both poison primers and target capture primers. In one aspect of the present disclosure is a method of enriching a plurality of target nucleic acid molecules, e.g., between about 1 and about 10000 target nucleic acid molecules, or between about 1 and about 5000 target nucleic acid molecules, or between about 1 and about 1000 target nucleic acid molecules, where the method utilizes both poison primers and target capture primers.

The present disclosure is also directed to methods of amplifying a target enriched sample, such as a target enriched sample prepared using any one of the methods described herein. Additionally, the present disclosure is also directed to methods of sequencing using a target enriched sample, such as a target enriched sample prepared using any one of the methods described herein. The methods of the present disclosure can be used as a part of a sequencing protocol, including a high throughput single molecule sequencing protocol. In some embodiments, the method of the present disclosure generates a library of enriched target nucleic acid molecules to be sequenced. The enriched target nucleic acid molecules in the library may optionally incorporate barcodes for molecular identification and sample identification, such as described in U.S. Publication No. 2020/0032244, and in U.S. Pat. Nos. 7,393,665, 8,168,385, 8,481,292, 8,685,678, and 8,722,368, the disclosures of which are hereby incorporated by reference herein in their entireties.

In some embodiments, the present disclosure describes a general approach for unidirectional dual probe primer extension-based enrichment that utilizes both poison primers and target capture primers. In some embodiments, the method comprises hybridizing a first target capture primer to a first target nucleic acid molecule in the library of nucleic acid molecules, wherein the first target capture primer comprises a capture moiety; hybridizing a first poison primer to a first one non-target nucleic acid molecule in the library of nucleic acid molecules, wherein the first poison primer does not include any capture moiety; extending both the first hybridized target capture primer and the first hybridized poison primer, wherein the extension of the first hybridized target capture primer provides a first target capture primer extension complex comprising the first target nucleic acid molecule and the extended first target capture primer; and enriching the first target nucleic acid molecule relative to the library of nucleic acid molecules in the library of nucleic acid molecules. In some embodiments, the introduced poison primer hybridizes and extends on a non-target nucleic acid molecule ("non-target nucleic acid molecule) and prevents or reduces mis-priming of a target capture primer with the non-target nucleic acid molecule. In other embodiments, the poison primer hybridizes upstream from a target capture primer which had been mis-primed and hybridized to a non-target nucleic acid molecule, and then extends and displaces a capture moiety from the mis-primed and hybridized target capture primer. It is believed that these two mechanisms of action may prevent or reduce downstream enrichment of mis-primed non-target nucleic acid molecules.

Figure 1B:
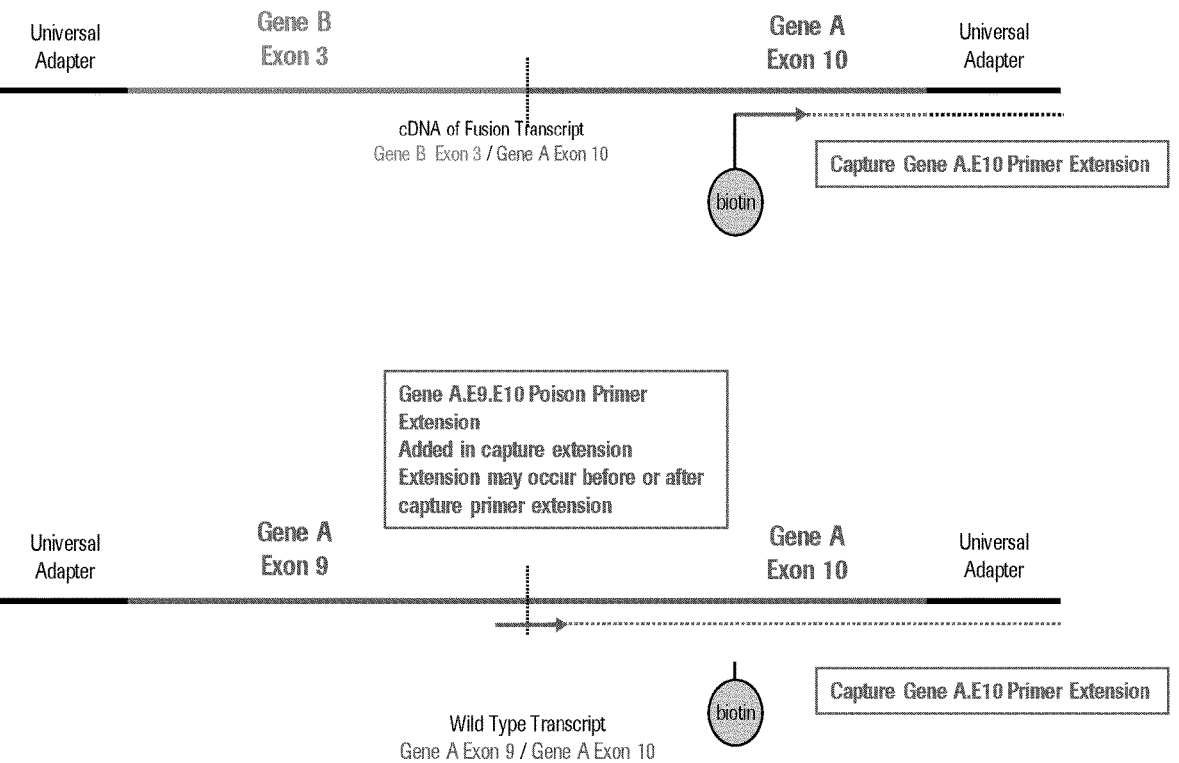
FIG. 1B provides an overview of the use of poison primers in conjunction with target capture primers to effectuate the enrichment of target nucleic acid molecules from next-generation sequencing capture libraries by depleting the library of background molecules. In some embodiments, the target nucleic acid molecules are fusion transcripts.

Advantageously, the compositions, kits, and methods of the present disclosure allow for the enrichment of low abundance target nucleic acid molecules in a nucleic acid library including the low abundance target nucleic acid molecules (e.g. mRNA; fusion transcripts) and high abundance non-target nucleic acid molecules (e.g. rRNA; wild-type transcripts). In some embodiments, the poison primers are utilized to effectuate the targeted depletion of undesired molecules, i.e. non-target nucleic acid molecules, from next-generation sequencing libraries. This may include rRNA-derived cDNA molecules, and other non-target molecules that are being captured undesirably and subsequently amplified downstream (see, e.g., FIG. 1A). Additionally, and in the context of a cDNA library, the compositions, kits, and methods of the present disclosure facilitate enrichment of the low abundance target molecules without the need for costly and time-consuming ribosomal depletion steps. In other embodiments, the poison primers are utilized to effectuate the enrichment of desired molecules from next-generation sequencing capture libraries by depleting the library of background molecules. For instance, this embodiment would include the depletion of wild-type transcripts when searching for novel fusion transcripts (see, e.g., FIG. 1B).

Figure 2A:
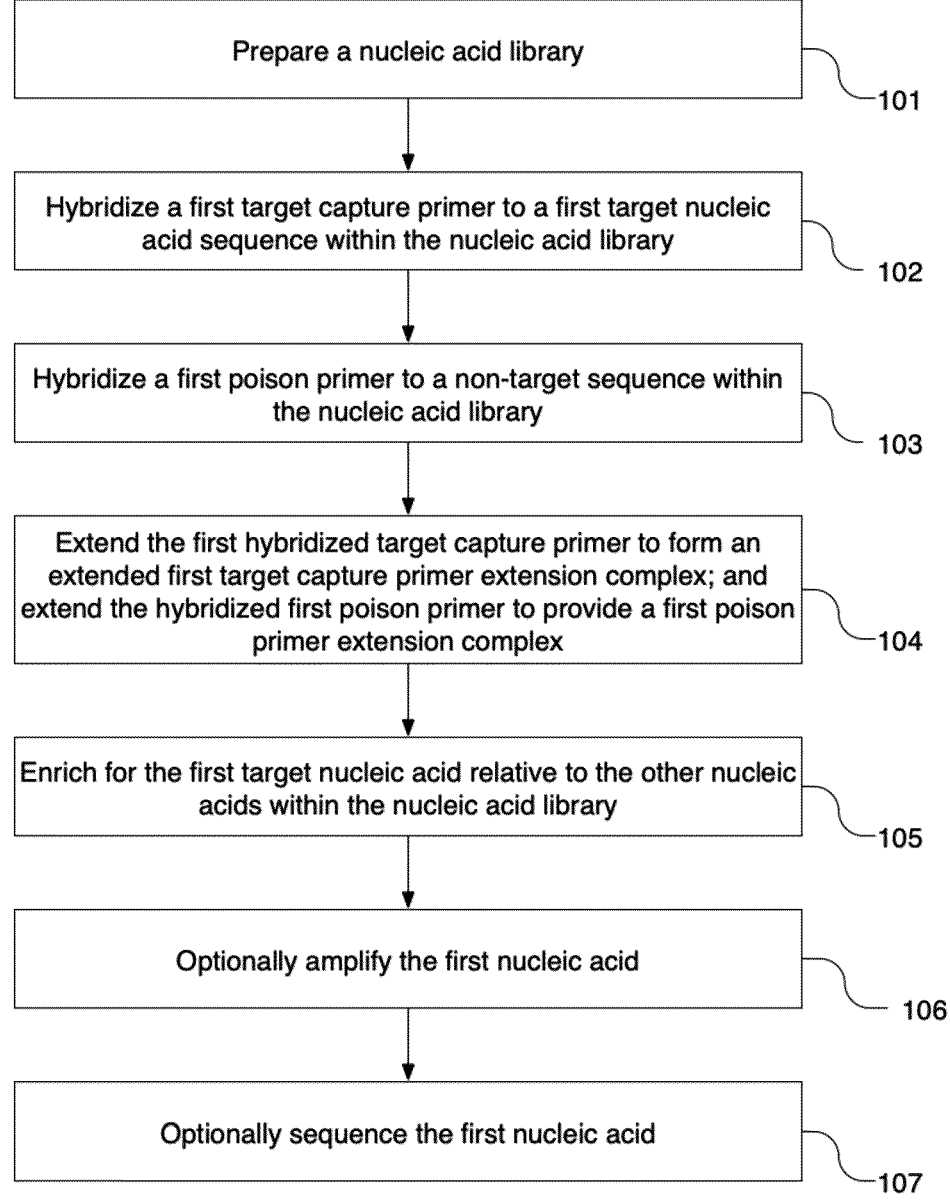
FIG. 2A illustrates an overview of a method of enriching for target nucleic acid molecules within a prepared nucleic acid library in accordance with one embodiment of the present disclosure.

With reference to FIG. 2A, in some embodiments, the methods disclosed herein comprise obtaining a nucleic acid library comprising a plurality of nucleic acid molecules (step 101). In some embodiments, the nucleic acid molecules within the obtained nucleic acid library are selected from DNA molecules, RNA molecules, genomic DNA molecules, cDNA molecules, mRNA molecules, rRNA molecules, mtDNA, siRNA molecules, or any combination thereof. In some embodiments, the plurality of nucleic acid molecules comprise single stranded polynucleotides. In some embodiments, the plurality of nucleic acid molecules are derived from a tissue sample, such as a tissue sample derived from a mammalian subject. In other embodiments, the plurality of nucleic acid molecules are derived from a cytology sample, such as a cytology sample derived from a mammalian subject.

In some embodiments, the obtained nucleic acid library includes a plurality of target nucleic acid molecules and/or a plurality of non-target nucleic acid molecules. In some embodiments, the non-target nucleic acid molecules are in high abundance as compared with the target nucleic acid molecules within the nucleic acid library. In some embodiments, the non-target nucleic acid molecules represent at least about 70% of the nucleic acid molecules in the obtained nucleic acid library. In other embodiments, the non-target nucleic acid molecules represent at least about 75% of the nucleic acid molecules in the obtained nucleic acid library. In yet other embodiments, the non-target nucleic acid molecules represent at least about 80% of the nucleic acid molecules in the obtained nucleic acid library. In further embodiments, the non-target nucleic acid molecules represent at least about 85% of the nucleic acid molecules in the obtained nucleic acid library. In yet further embodiments, the non-target nucleic acid molecules represent at least about 90% of the nucleic acid molecules in the obtained nucleic acid library. In even further embodiments, the non-target nucleic acid molecules represent at least about 95% of the nucleic acid molecules in the obtained nucleic acid library. In some embodiments, the non-target nucleic acid molecules represent at least about 96% of the nucleic acid molecules in the obtained nucleic acid library. In some embodiments, the non-target nucleic acid molecules represent at least about 97% of the nucleic acid molecules in the obtained nucleic acid library. In some embodiments, the non-target nucleic acid molecules represent at least about 98% of the nucleic acid molecules in the obtained nucleic acid library. In some embodiments, the non-target nucleic acid molecules represent at least about 99% of the nucleic acid molecules in the obtained nucleic acid library.

In some embodiments, the obtained nucleic acid library is a cDNA library which comprises mRNA derived molecules and at least about 90% rRNA. In some embodiments, the obtained nucleic acid library is a cDNA library which comprises mRNA derived molecules and at least about 92% rRNA. In other embodiments, the obtained nucleic acid library is a cDNA library which comprises mRNA derived molecules and at least about 94% rRNA. In yet other embodiments, the obtained nucleic acid library is a cDNA library which comprises mRNA derived molecules and at least about 95% rRNA. In further embodiments, the obtained nucleic acid library is a cDNA library which comprises mRNA derived molecules and at least about 96% rRNA. In further embodiments, the obtained nucleic acid library is a cDNA library which comprises mRNA derived molecules and at least about 97% rRNA. In further embodiments, the obtained nucleic acid library is a cDNA library which comprises mRNA derived molecules and at least about 98% rRNA. In further embodiments, the obtained nucleic acid library is a cDNA library which comprises mRNA derived molecules and at least about 99% rRNA. In some embodiments, the cDNA library includes rRNA and mRNA derived molecules, and wherein the cDNA library is derived from a biological sample that was not previously treated with a ribosomal depletion method. In some embodiments, it is desirable to enrich for the mRNA derived molecules without having to perform a ribosomal depletion step.

In some embodiments, the obtained nucleic acid library comprises fusion transcripts and wild-type transcripts. In some embodiments, the fusion transcripts are in low abundance as compared with the wild-type transcripts. In some embodiments, a ratio of fusion transcripts to wild-type transcripts in the obtained nucleic acid library is at least about 1:3. In other embodiments, a ratio of fusion transcripts to wild-type transcripts in the obtained nucleic acid library is at least about 1:4. In other embodiments, a ratio of fusion transcripts to wild-type transcripts in the obtained nucleic acid library is at least about 1:5. In other embodiments, a ratio of fusion transcripts to wild-type transcripts in the obtained nucleic acid library is at least about 1:10. In other embodiments, a ratio of fusion transcripts to wild-type transcripts in the obtained nucleic acid library is at least about 1:20. In other embodiments, a ratio of fusion transcripts to wild-type transcripts in the obtained nucleic acid library is at least about 1:50. In other embodiments, a ratio of fusion transcripts to wild-type transcripts in the obtained nucleic acid library is at least about 1:100.

In some embodiments, the obtained nucleic acid library is derived from one or more tumor samples and the target nucleic acid molecules include low abundance fusion transcripts. Non-limiting examples of fusion transcripts for detection include EML4-ALK, ETV6-NTRK3 and ALK-RET fusion oncogenes. In other embodiments, the obtained nucleic acid library includes expressed housekeeping genes, where the expressed housekeeping genes are in low abundance relative to non-target nucleic acid molecules within the obtained nucleic acid library. Non-limiting examples of housekeeping genes include VCP, RAB7A and CHMP2A.

In some embodiments, nucleic acid fragments are first prepared from a biological sample, e.g., a tissue sample and/or a cytology sample. The DNA sequencing library may be constructed from genomic DNA for genome analysis, or from cDNA prepared from RNA or mRNA for transcriptome analysis, and it may be constructed from the DNA or cDNA of any species of organism from which these nucleic acids can be extracted. In some embodiments, the obtained sample is sheared into fragments to provide a population of nucleic acid fragments. In some embodiments, shearing of the obtained genomic sample is effectuated using mechanical (e.g., nebulization or sonication) and/or enzymatic fragmentation (e.g., restriction endonucleases). In some embodiments, the generated nucleic acid fragments are randomly sized. In some embodiments, the generated nucleic acid fragments have a length which are less than about 1000 base pairs. In other embodiments, the generated nucleic acid fragments comprises sequence fragments having a sequence size ranging from between about 100 to about 1000 base pairs in length. In yet other embodiments, the generated nucleic acid fragments comprises sequence fragments having a sequence size ranging from between about 500 to about 750 base pairs in length.

In some embodiments, adapters are then added via a ligation reaction to the population of nucleic acid molecules. In some embodiments, the adapters include one or more barcode sequences. Methods of ligating adapters to a nucleic acid molecule are described in U.S. Patent Publication Nos. 2017/0037459, 2018/0334709, 2018/0016630 and in PCT Publication No. WO2017021449, the disclosures of which are hereby incorporated by reference herein in their entireties.

Following the fragmentation and the preparation of the nucleic acid library (step 101), a pool of primers are introduced to the nucleic acid library or to a reaction mixture including the nucleic acid library and other components to effectuate hybridization (e.g. buffers, etc.). Following their introduction, the one or more poison primers and the one or more target capture primers in the pool of primers at least partially hybridize to one or more non-target and/or target nucleic acid molecules, respectively (steps 102 and 103).

In some embodiments, the pool of primers includes one or more poison primers and one or more target capture primers. In some embodiments, the pool of primers includes between about 1 to about 1000 different poison primers. In some embodiments, the pool of primers includes between about 50 to about 750 different poison primers. In other embodiments, the pool of primers includes between about 100 to about 500 different poison primers. In some embodiments, the pool of primers includes between about 50 to about 2500 different target capture primers. In other embodiments, the pool of primers includes between about 150 to about 1000 different target capture primers.

In some embodiments, the one or more target capture primers are target-specific and, thus, designed to hybridize to a subset of complementary nucleic acid molecules within the nucleic acid library which include desired target genes, exons, and/or other genomic regions of interest (herein after referred to as "target nucleic acid molecules"). In some embodiments, the target capture primers include a pool of Roche SeqCap EZ Probes (available from Roche Sequencing and Life Sciences, Indianapolis, IND). In some embodiments, the target capture primers include a pool of Ampliseq primers, available from ThermoFisher.

In some embodiments, the target capture primers mays be comprised of ribonucleic acids, deoxyribonucleic acids, or other nucleic acid analogs known in the art. In some embodiments, the target capture primers may include one or more non-natural nucleotides, e.g., locked nucleic acid (LNA), peptide nucleic acid (PNA), gamma-PNA, as glycol nucleic acid (GNA), and threose nucleic acid (TNA). In some embodiments, the target capture primers have a length ranging from between about 20 nucleotides to about 100 nucleotides. In other embodiments, the target capture primers have a length ranging from between about 40 nucleotides to about 80 nucleotides. In yet other embodiments, the target capture primers have a length ranging from between about 50 nucleotides to about 75 nucleotides.

In some embodiments, each of the one or more target capture primers are conjugates comprising (i) a capture moiety; and (ii) a sequence that is substantially complementary to a sequence of the one or more target nucleic acid molecules in the nucleic acid library. In some embodiments, each of the one or more target capture primers are capable of binding to a functionalized substrate through the capture moiety after hybridization and/or extension and as described herein (see, e.g., FIGS. 3A and 4). In other embodiments, the target capture primers are bound to a functionalized substrate through the capture moiety prior to hybridization as described herein (see, e.g., FIGS. 5 and 6).

In some embodiments, the capture moiety of each the one or more target capture primers comprises a first moiety (e.g., a first reactive functional group) which is reactive with a second moiety (e.g., a second reactive functional group) of another entity (e.g., a second moiety conjugated to a functionalized substrate). In some embodiments, the first moiety is a first member of a pair of specific binding entities; and the second moiety is a second member of the same pair of specific binding entities. In some embodiments, a "reaction"

between a first moiety and a second moiety may mean that a covalent linkage is formed between two reactive groups or two reactive functional groups of the two moieties; or may mean that the two reactive groups or two reactive functional groups of the two moieties associate with each other, interact with each other, hybridize to each other, hydrogen bond with each other, etc. In some embodiments, the "reaction" thus includes binding events, such as the binding of a hapten with an anti-hapten antibody, or the binding of biotin with strepta-vidin. In some embodiments, each of the target capture primers includes the same capture moiety, e.g., biotin. In other embodiments, different subsets of target capture primers include different capture moieties.

In some embodiments, the capture moiety may include biotin to bind to a functionalized substrate including avidin or streptavidin. In other embodiments, the capture moiety may include a thiolated molecule to bind to a functionalized substrate which includes gold particles. In yet other embodiments, the capture moiety may include an amine-terminated molecule to bind to an NHS-activated substrate.

In some embodiments, the capture moiety includes immo-bilized antibodies, which may be used to bind to molecules including or conjugated to specific antigenic molecules, such as an antigenic molecule bound to a functionalized substrate. In other embodiments, the capture moiety includes an antigenic molecule which may be used to bind to an immobilized antibodies, such as an antibody bound to a functionalized substrate.

In some embodiments, the capture moiety includes enzymes, which may be used to bind to molecules including or conjugated to specific enzyme substrates. In other embodiments, the capture moiety includes a substrate for an enzyme, which may be used to bind to an enzyme, such as an enzyme coupled to a functionalized substrate.

In some embodiments, the capture moiety includes recep-tors, which may be used to bind to molecules including or conjugated to specific receptor ligands, such as a receptor ligand bound to a functionalized substrate. In other embodi-ments, the capture moiety includes one or more receptor ligands, which may be used to bind to molecules including receptors, such as receptors bound to a functionalized sub-strate.

In some embodiments, the capture moiety includes lec-tins, which may be used to bind to molecules including or conjugated to specific polysaccharides, such as a polysac-charide bound to a functionalized substrate. In other embodiments, the capture moiety includes one or more polysaccarides, which may be used to bind to molecules including or conjugated to one or more lectins, such as one or more lectins bound to a functionalized substrate.

In even further embodiments, the capture moiety includes one or more nucleic acid sequences which may be used to bind to molecules including or conjugated to complementary base sequences. In other embodiments, the capture moiety may include tethered DNA/RNA aptamers which may spe-cifically bind to target analytes such as small molecules, peptides, proteins, cells.

Each of the one or more poison primers are designed to hybridize to a second subset of complementary nucleic acid molecules within the nucleic acid library which do not include the desired genes, exons, and/or other genomic regions of interest (hereinafter referred to as "non-target nucleic acid molecules"). Unlike the target capture primers, the poison primers of the present disclosure are not conju-gated to any capture moiety, and thus are not capable to reacting with any functionalized substrate.

In some embodiments, the poison primers mays be com-prised of ribonucleic acids, deoxyribonucleic acids, or other nucleic acid analogs known in the art. In some embodi-ments, the poison primers may include one or more non-natural nucleotides, e.g., locked nucleic acid (LNA), peptide nucleic acid (PNA), gamma-PNA, as glycol nucleic acid (GNA), and threose nucleic acid (TNA). In some embodi-ments, the poison primers have a length ranging from between about 20 nucleotides to about 100 nucleotides. In other embodiments, the poison primers have a length rang-ing from between about 40 nucleotides to about 80 nucleo-tides. In yet other embodiments, the poison primers have a length ranging from between about 50 nucleotides to about 75 nucleotides.

In some embodiments, the poison primers have a lower melting temperature ($T_m$) as compared with the target cap-ture primers. In some embodiments, the $T_m$ of the poison primers is at least about 2% lower than the $T_m$ of the target capture primers. In other embodiments, the $T_m$ of the poison primers is at least about 5% lower than the $T_m$ of the target capture primers. In yet other embodiments, the $T_m$ of the poison primers is at least about 10% lower than the $T_m$ of the target capture primers. In further embodiments, the $T_m$ of the poison primers is at least about 15% lower than the $T_m$ of the target capture primers. In even further embodiments, the $T_m$ of the poison primers is at least about 20% lower than the $T_m$ of the target capture primers.

In some embodiments, the first target capture primer has a melting temperature which is at least about 1° C. greater than the melting temperature of the first poison primer. In other embodiments, the first target capture primer has a melting temperature which is at least about 2° C. less than the melting temperature of the first poison primer. In yet other embodiments, the first target capture primer has a melting temperature which is at least about 3° C. greater than the melting temperature of the first poison primer. In further embodiments, the first target capture primer has a melting temperature which is at least about 4° C. greater than the melting temperature of the first poison primer. In even further embodiments, the first target capture primer has a melting temperature which is at least about 5° C. greater than the melting temperature of the first poison primer. In further embodiments, the first target capture primer has a melting temperature which is at least about 6° C. greater than the melting temperature of the first poison primer. In further embodiments, the first target capture primer has a melting temperature which is at least about 7° C. greater than the melting temperature of the first poison primer. In further embodiments, the first target capture primer has a melting temperature which is at least about 8° C. greater than the melting temperature of the first poison primer. In further embodiments, the first target capture primer has a melting temperature which is at least about 9° C. greater than the melting temperature of the first poison primer. In further embodiments, the first target capture primer has a melting temperature which is at least about 10° C. greater than the melting temperature of the first poison primer.

In some embodiments, the $T_m$ of the poison primer is at least about 50° C. In some embodiments, the $T_m$ of the poison primer is at least about 55° C. In some embodiments, the $T_m$ of the poison primer is at least about 60° C. In some embodiments, the $T_m$ of the poison primer is at least about 65° C. In some embodiments, the $T_m$ of the poison primer is at least about 70° C. In some embodiments, the $T_m$ of the poison primer is at least about 75° C. In some embodiments, the $T_m$ of the poison primer is at least about 80° C.

In some embodiments, the concentration of target capture primer and the concentration of the poison primer is about the same. In other embodiments, the concentration of the target capture primer and the concentration of the poison primer are different. In some embodiments, the concentration of the poison primer is at least two times greater than the concentration of the target capture primer. In other embodiments, the concentration of the poison primer is at least five times greater than the concentration of the target capture primer. In other embodiments, the concentration of the poison primer is at least ten times greater than the concentration of the target capture primer. In other embodiments, the concentration of the poison primer is at least twenty times greater than the concentration of the target capture primer. In other embodiments, the concentration of the poison primer is at least fifty times greater than the concentration of the target capture primer. In other embodiments, the concentration of the poison primer is at least one-hundred times greater than the concentration of the target capture primer. In other embodiments, the concentration of the poison primer is at least two hundred times greater than the concentration of the target capture primer. In other embodiments, the concentration of the poison primer is at least five-hundred times greater than the concentration of the target capture primer. In some embodiments, one or more target capture primers may mis-prime, i.e. hybridize to a non-target nucleic acid molecule as opposed to a target nucleic acid molecule. Mis-priming events are illustrated in FIGS. 3A and 4-6 herein. It is believed that the introduction, hybridization, and/or extension of one or more poison primers prevents and/or mitigates mis-priming events. Moreover, it is believed that should mis-priming occur, that the extension of a hybridized poison primer would may prevent and/or mitigate the subsequent capture and/or enrichment of a non-target nucleic acid molecule.

Following the hybridization of the one or more target capture primers to the one or more target nucleic acid molecules (step 102) and the hybridization of the one or more poison primers to the one or more non-target nucleic acid molecules (step 103), each of the one or more hybridized target capture primers and the one or more hybridized poison primers are extended (step 104) to form one or more extended target capture primer complexes and/or one or more extended poison primer complexes. In those instances where a target capture primer is mis-primed, the mis-primed and hybridized target capture primer will extend be extended along the non-target nucleic acid molecule as further illustrated herein (see, e.g., FIGS. 3A and 4-6).

In some embodiments, the one or more hybridized target capture primers are extended through the use of a first polymerase, thus forming one or more double-stranded products, each comprising a target nucleic acid molecule hybridized to an extended target capture primer. In some embodiments, each of the one or more extended target capture primer complexes includes an extended target capture primer (which itself includes the hybridized target capture primer including the capture moiety) and the target nucleic acid sequence to which the target capture primer hybridized to. In some embodiments, the extended target capture primer includes the reverse complement of at least a portion of the target nucleic acid molecule to which the target capture primer hybridized to.

In those instances where one or more target capture primers are mis-primed, those mis-primed target capture primers may also be extended using the first polymerase. In some embodiments, the one or more mis-primed hybridized target capture primers (hybridized to the non-target nucleic acid molecules) are extended through the use of a first polymerase, thus forming one or more double-stranded products, each comprising a non-target nucleic acid molecule hybridized to an extended target capture primer.

Likewise, the one or more hybridized poison primers are extended through the use of a second polymerase, thus forming one or more double-stranded products, each comprising a non-target nucleic acid molecule hybridized to an extended poison primer. In some embodiments, each of the one or more extended poison primer complexes includes an extended target capture primer and the non-target nucleic acid sequence to which the poison primer hybridized to. In some embodiments, the extended poison primer includes the reverse complement of at least a portion of the non-target nucleic acid molecule to which the poison primer hybridized to.

In some embodiments, the first polymerase used to extend the one or more hybridized target capture primers is the same as the second polymerase used to extend the one or more hybridized poison primers. In other embodiments, the first polymerase used to extend the one or more hybridized target capture primers is different than the second polymerase used to extend the one or more hybridized poison primers. Depending on the type of nucleic acid molecule being analyzed, the polymerase may be a DNA-dependent DNA polymerase ("DNA polymerase") or an RNA-dependent DNA polymerase ("reverse transcriptase"). Suitable polymerases are selected from a Taq or Taq-derived polymerase (e.g., KAPA 2G polymerase from KAPA BIOSYSTEMS); or a B-family DNA polymerase (e.g., KAPA HIFI polymerase from KAPA BIOSYSTEMS).

In some embodiments, the hybridization and extension processes (steps 102, 103, and 104) are performed simultaneously. In other embodiments, the hybridization and extension processes (steps 102, 103, and 104) are performed sequentially. In some embodiments, the length of the extensions of the one or more hybridized target capture primers and the one or more hybridized poison primers may be controlled actively through techniques such as inactivating the first and/or second polymerases added, or passively by enabling the reaction to go to completion such as through the consumption of limiting reactants. Such methods are further described in U.S. Patent Publication No. 2020/0032244, the disclosure of which is hereby incorporated by reference herein in its entirety.

Referring again to FIG. 2A, following the extending of both the hybridized target capture primers and the hybridized poison primers (step 104), the nucleic acid library is enriched for the presence of the one or more target nucleic acid molecules. In some embodiments, enrichment involves increasing the concentration of the one or more target nucleic acid molecules through depletion (i.e., removal) of other members of the library of nucleic acid molecules that are not target nucleic acid molecules. In some embodiments, enrichment includes the step of forming one or more release primer extension complexes.

Figure 2B:
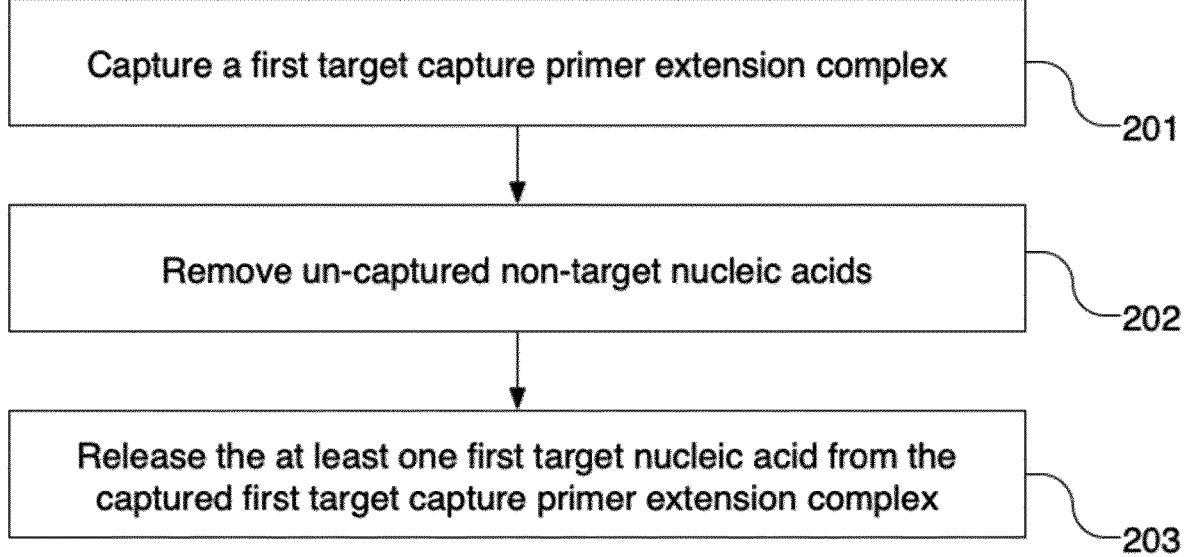
FIG. 2B illustrates a method of enriching for target nucleic acid molecules within a prepared nucleic acid library in accordance with one embodiment of the present disclosure.

One method of target nucleic acid molecule enrichment is illustrated in FIG. 2B. For instance, at step 201 the one or more target capture primer extension complexes are captured. Capture of the one or more target capture primer extension complexes may be achieved in a variety of ways as disclosed herein and can be achieved prior to, concurrent with, or subsequent to either of the hybridization and/or extension steps described above.

In some embodiments, capturing comprises contacting the target capture primer extension complexes with an appropriately functionalized substrate (e.g., beads) after the step of hybridization and/or extension such that the capture moiety of each target capture primer extension complex reacts with a corresponding moiety of the functionalized substrate, thereby binding the one or more target capture primer extension complexes to the functionalized substrate. For example, a target capture primer extension complex may include a capture moiety comprising biotin which would bind to a functionalized substrate including streptavidin. In those embodiments where the capture moiety is coupled to a functionalized substrate (e.g. beads) prior to the step of hybridization (i.e., prior to step 102), capture is effectuated through the hybridization of each target capture primer to its corresponding target nucleic acid. Other methods of capturing target capture primer extension complexes are described further herein and also described in U.S. Publication No. 2020/0032244, the disclosure of which is hereby incorporated by reference herein in its entirety.

In some embodiments, the functionalized substrate comprises beads having an appropriately functionalized surface (where the substrate may be functionalized with any of the moieties described above). In some embodiments, the beads are included within a column or a microfluidic device. In some embodiments, the beads are magnetic beads. In other embodiments, the beads are non-magnetic beads.

Following the capture of the one or more target capture primer extension complexes, one or more purification process are performed such that non-target nucleic acid molecules, as well as any other unused reaction components (e.g. nucleotides, primer molecules, enzymes, buffers, etc.), are removed (step 202). For instance, the non-target nucleic acid molecules may be removed by flowing a wash fluid and/or buffer through a column including the functionalized substrate (e.g., a column including a plurality of beads having an appropriately functionalized surface). In some embodiments, washing is performed at least one. In other embodiments, washing is performed at least twice. In yet other embodiments, washing is performed at least three times. The skilled artisan will appreciate that the one or more target capture primer extension complexes bound to the functionalized substrates (e.g. beads) will remain bound to the functionalized substrates as the wash fluid and/or buffer is flowed through the column housing the functionalized substrate, while those unbound non-target nucleic acid molecules will be washed away, resulting in a reaction mixture enriched with the one or more target nucleic acid molecules.

In some embodiments, the target nucleic acid molecules may be optionally amplified following enrichment. In some embodiments, the captured target nucleic acid molecules are directly amplified while coupled to the functionalized surface. Such methods are described in U.S. Pat. Nos. 10,240, 192, 10,160,995, and 7,842,457, the disclosures of which are hereby incorporated by reference herein in their entireties. In other embodiments, the one or more target nucleic acid molecules are released from the captured target capture primer extension complexes (step 203) prior to amplification step.

Figure 2C:
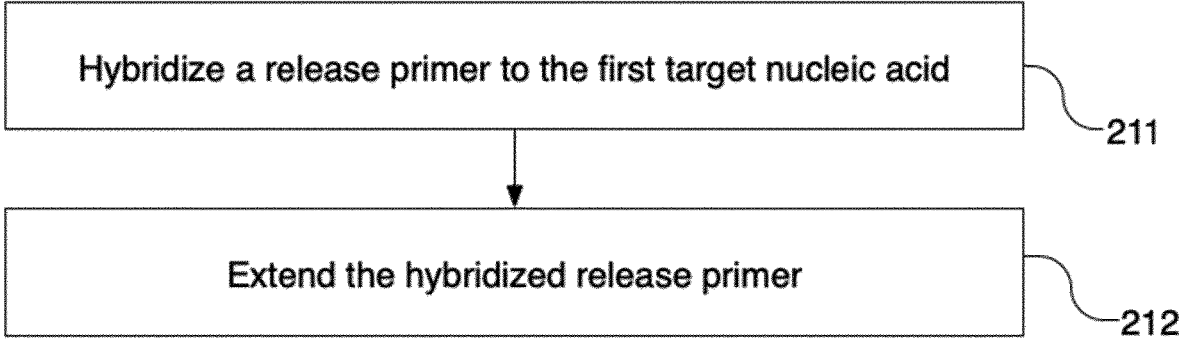
FIG. 2C illustrates a method of liberating a target nucleic acid molecule from a formed complex comprising at least a portion of the target nucleic acid molecule and an extended hybridized target capture primer in accordance with one embodiment of the present disclosure.

In some embodiments, the release of the one or more target nucleic acid molecules follows the workflow set forth in FIG. 2C. For example, in some embodiments, one or more release primers are hybridized to the one or more target nucleic acid molecules (step 211). In some embodiments, the one or more release primers are designed to hybridize to a portion of the one or more target nucleic acid molecules and between the first and second adapters. In other embodiments, the one or more release primers are designed to hybridize to portions of the target nucleic acid molecules which are upstream relative to the one or more target capture primer extension complexes. In some embodiments, the primer design algorithm is designed to pick primers as close as possible to the capture primer. In some examples there is no gap between capture and release primers. In some embodiments, the release primer will not have the capture moiety, similar to the poison primer. It will however have a Tm similar to the capture primer.

Next, the one or more hybridized release primers are extended using a polymerase, thereby forming one or more extended hybridized release primers (step 212). In some embodiments, the extension of the one or more hybridized release primers with the polymerase liberates the one or more target extended target capture primers from one or more target capture primer extension complexes. In some cases, the polymerase exhibits strand displacement activity. In some cases, the polymerase exhibits 5'-3' exonuclease activity that digests a single strand of a double-stranded nucleic acid molecule (referred to herein as 5'-3' double-stranded exonuclease activity) or double-stranded exonuclease activity. In some cases, the polymerase exhibits both strand displacement and 5'-3' double-stranded exonuclease activity. In some cases, the strand displacement, 5'-3' double-stranded exonuclease activity, or combination thereof, can displace a target nucleic acid molecule (e.g., original target nucleic acid molecule from a provided sample) into solution.

For example, in some embodiments, a first double-stranded product containing the target nucleic acid molecule hybridized to the extended target capture primer is immobilized on a functionalized substrate, e.g., by affinity capture of a ligand (e.g., biotin or a derivative thereof) through the capture moiety of the extended target capture primer. In such embodiments, the strand displacement activity of the polymerase that extends the hybridized release primer displaces the target nucleic acid molecule from the sample into solution. Alternatively, 5'-3' exonuclease activity can degrade extended target capture primer that is immobilized by affinity capture and hybridized to target nucleic acid molecule, wherein the 5'-3' exonuclease activity thereby releases the target nucleotide into solution. Additional methods of liberating a target nucleic acid molecule from a formed target capture primer extension complex are described in US. Patent Publication No. 2018/0016630, the disclosure of which is hereby incorporated by reference herein in its entirety.

The released one or more target nucleic acid molecules may then be used in one or more downstream processes, e.g. sequencing, amplification, further coupling, etc. Referring again to FIG. 2A, in some embodiments, the nucleic acid library enriched with the one or more target nucleic acid molecules is optionally amplified (step 106). In some embodiments, the step of optional amplification (106) comprises one of a linear or exponential amplification (e.g., polymerase chain reaction (PCR)). As used herein, "PCR" refers to a reaction for the in vitro amplification of specific DNA sequences by the simultaneous primer extension of complementary strands of DNA. As used herein, PCR encompass derivative forms of the reaction, including but not limited to, RT-PCR, real-time PCR, nested PCR, quantitative PCR, multiplexed PCR, digital PCR, digital droplet PCR, and assembly PCR. Amplification of the target nucleic acid molecules following enrichment may comprise non-PCR based methods. Non-limiting examples of non-PCR based methods include nucleic acid sequence-based amplification (NASBA), transcription-mediated amplification (TMA), whole transcriptome amplification (WTA), whole genome amplification (WGA), multiple displacement amplification (MDA), strand displacement amplification (SDA), real-time SDA, rolling circle amplification, and/or circle-to-circle amplification.

In general, amplification (step 106) comprises amplifying the target nucleic acid molecule with a polymerase, a first amplification primer, and a second amplification primer. In some embodiments, the first and second amplification primers are designed to be complementary to the sequences of the adapters incorporated into the one or more target nucleic acid molecules in the library of nucleic acid molecules in the step 101. For example, the first amplification primer may have a 3' end complementary to the first adapter and the second amplification primer may have a 3' end complementary to the second adapter. In some embodiments, the amplification primers may include any sequences that are present within the target nucleic acid molecule being amplified (e.g., gene/target specific primers, universal primers, or the like) and can support synthesis of one or both strands (i.e., both the top and bottom strands of a double-stranded nucleic acid molecules corresponding to the template of the amplification reaction). In some embodiments, the first and second amplification primers are universal primers. Additional methods of amplification are described in U.S. Publication Nos. 2020/0032244 and 2018/0016630, the disclosures of which are hereby incorporated by reference herein in their entireties.

In some embodiments, sequencing may be optionally performed according to any method known to those of ordinary skill in the art (see step 107 of FIG. 2A). In some embodiments, sequencing methods include Sanger sequencing and dye-terminator sequencing, as well as next-generation sequencing technologies such as pyrosequencing, nanopore sequencing, micropore-based sequencing, nanoball sequencing, MPSS, SOLiD, Illumina, Ion Torrent, Starlite, SMRT, tSMS, sequencing by synthesis, sequencing by ligation, mass spectrometry sequencing, polymerase sequencing, RNA polymerase (RNAP) sequencing, microscopy-based sequencing, microfluidic Sanger sequencing, microscopy-based sequencing, RNAP sequencing, etc. Instruments and methods of sequencing are disclosed, for example, in PCT Publication Nos. WO2014144478, WO2015058093, WO2014106076 and WO2013068528, the disclosures of which are hereby incorporated by reference in their entireties.

In some embodiments, sequencing (step 107) can be performed by a number of different methods, such as by employing sequencing by synthesis technology. Sequencing by synthesis according to the prior art is defined as any sequencing method which monitors the generation of side products upon incorporation of a specific deoxynucleoside-triphosphate during the sequencing reaction (Hyman, 1988, Anal. Biochem. 174:423-436; Rhonaghi et al., 1998, Science 281:363-365). One prominent embodiment of the sequencing by synthesis reaction is the pyrophosphate sequencing method. In this case, generation of pyrophosphate during nucleotide incorporation is monitored by an enzymatic cascade which results in the generation of a chemo-luminescent signal. The 454 Genome Sequencer System (Roche Applied Science cat. No. 04 760 085 001), an example of sequence by synthesis, is based on the pyrophosphate sequencing technology. For sequencing on a 454 GS20 or 454 FLX instrument, the average genomic DNA fragment size is in the range of 200 or 600 bp, respectively, as described in the product literature.

In some embodiments, a sequencing by synthesis reaction can alternatively be based on a terminator dye type of sequencing reaction. In this case, the incorporated dye deoxynucleotriphosphates (ddNTPs) building blocks comprise a detectable label, which is preferably a fluorescent label that prevents further extension of the nascent DNA strand. The label is then removed and detected upon incorporation of the ddNTP building block into the template/primer extension hybrid for example by using a DNA polymerase comprising a 3'-5' exonuclease or proofreading activity.

In some embodiments, and in the case of the Genome Sequencer workflow (Roche Applied Science Catalog No. 04 896 548 001), in a first step, (clonal) amplification is performed by emulsion PCR. Thus, it is also within the scope of the present disclosure, that the step of amplification is performed by emulsion PCR methods. The beads carrying the clonally amplified target nucleic acid molecules may then become arbitrarily transferred into a picotiter plate according to the manufacturer's protocol and subjected to a pyrophosphate sequencing reaction for sequence determination.

In some embodiments, sequencing is performed using a next-generation sequencing method such as that provided by Illumina, Inc. (the "Illumina Sequencing Method"). Without wishing to be bound by any particular theory, the Illumina next-generation sequencing technology uses clonal amplification and sequencing by synthesis (SBS) chemistry to enable rapid, accurate sequencing. The process simultaneously identifies DNA bases while incorporating them into a nucleic acid chain. Each base emits a unique fluorescent signal as it is added to the growing strand, which is used to determine the order of the DNA sequence.

As noted above, it is desirable to prevent target capture primers from inadvertently "mis-priming," i.e., from binding to non-target sequences. The ability of poison primers to prevent or reduce "mis-priming" ab initio is illustrated in a first non-limiting embodiment in FIG. 3A. The ability of poison primers to prevent or reduce capture of non-target molecules that have been mis-primed is illustrated in a second non-limiting embodiment in FIG. 4. In general, each of these two embodiments illustrates a method of primer extension target enrichment including in-solution primer-mediated capture of a target nucleic acid molecule, followed by enrichment of the captured target nucleic acid molecule relative to other nucleic acid molecules present in a library of nucleic acid molecules.

Figure 3A:
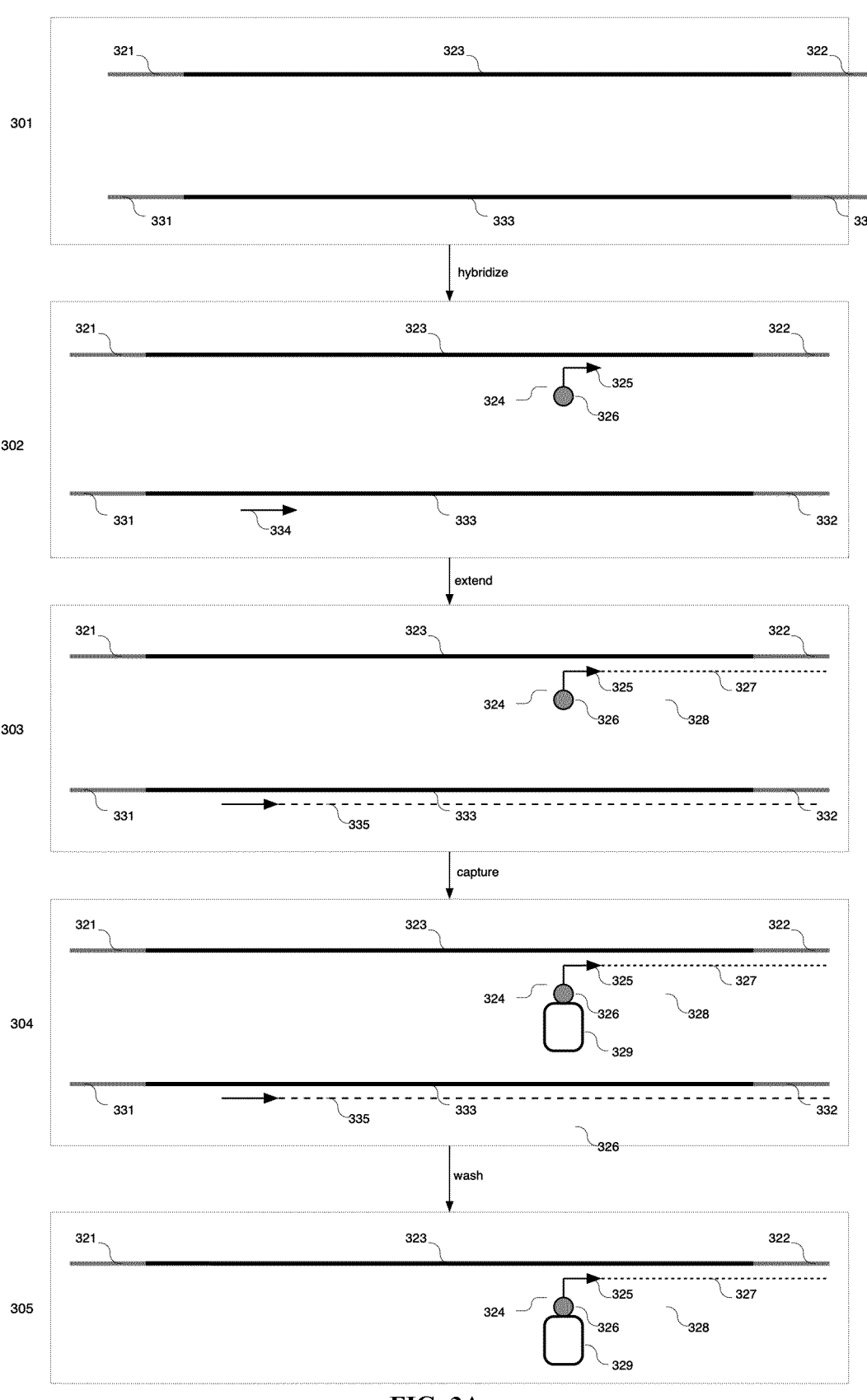
FIG. 3A illustrates a method of primer extension target enrichment where the hybridization to and extension of a poison primer along a non-target nucleic acid molecule prevents or reduces the incidence of mis-priming of a target capture primer to the non-target nucleic acid in accordance with one embodiment of the present disclosure.

FIG. 3A depicts a method of target nucleic acid molecule enrichment where an extended poison primer prevents or reduces the incidence of mis-priming of a target capture primer. In this embodiment, the extension of a hybridized poison primer prevents a target capture primer from hybridizing to the non-target nucleic acid molecule. Turning first to panel 301 of FIG. 3A, a library of nucleic acid molecules is first prepared, where the library of nucleic acid molecules includes one or more target nucleic acid molecules 323 and one or more non-target nucleic acid molecules 333. In some embodiments, the one or more target nucleic acid molecules 323 are in low abundance as compared with the one or more non-target nucleic acid molecules in the nucleic acid molecule library. For example, in some embodiments the one or more target nucleic acid molecules may represent less than about 10% of the nucleic acid molecules in the nucleic acid molecule library. In other embodiments the one or more target nucleic acid molecules may represent less than about 5% of the nucleic acid molecules in the nucleic acid molecule library. In some embodiments, adapters (321, 322, 331, and 332) are ligated to both ends of the one or more target nucleic acid molecules 323 and the one or more non-target nucleic acid molecules 333.

Panel 301 illustrates a target nucleic acid molecule 323, where the target nucleic acid molecule includes a first end comprising a first adapter 301 and a second end comprising a second adapter 322. Panel 301 further illustrates a non-target nucleic acid molecule 333, where the non-target nucleic acid molecule includes a first end comprising a first adapter 331 and a second end comprising a second adapter 333. The first adapters 321 and 331 are located at the 5' ends of the target and non-target nucleic acid molecules, respectively. The second adapters 322 and 332 are located at the 3' ends of the target and non-target nucleic acid molecules, respectively. In some embodiments, the first adapters 321 and 331 are the same; likewise, in some embodiments the second adapters 331 and 332 are the same.

Following the preparation of the nucleic acid library, one or more target capture primers 324 and one or more poison primers 334 are hybridized to the target and non-target nucleic acid molecules 323 and 333, respectively (see panel 302). In some embodiments, the one or more target capture primers 324 each include a target capture region 325 that is complementary to at least a portion of the target nucleic acid molecule 323 and a capture moiety 326. The capture moiety may include any of those moieties described above. In some embodiments, the capture moiety is biotin. In some embodiments, the one or more poison primers 334 include a non-target specific region that is complementary to at least a portion of the non-target nucleic acid molecule 333. Notably, the one or more poison primers 334 do not include a capture moiety, and thus are not capable of being captured during any enrichment step.

As shown in panel 303 of FIG. 3A, each of the one or more hybridized target capture primers and the one or more poison primers are extended. In some embodiments, the one or more hybridized target capture primers 324 are extended with a first polymerase (not shown), thereby producing one or more target capture primer extension complexes 328. The one or more target capture primer extension complexes 328 each include a target nucleic acid molecule 323 and an extended target capture primer 327 (where the dashed line indicates the extended portion of a hybridized target capture primer 324). As further illustrated in panel 303, the one or more hybridized poison primers 334 are extended with a second polymerase (not shown), thereby producing one or more extended poison primers 335 (where the dashed line again indicates the extended portion of the hybridized poison primer 334).

Figure 4:
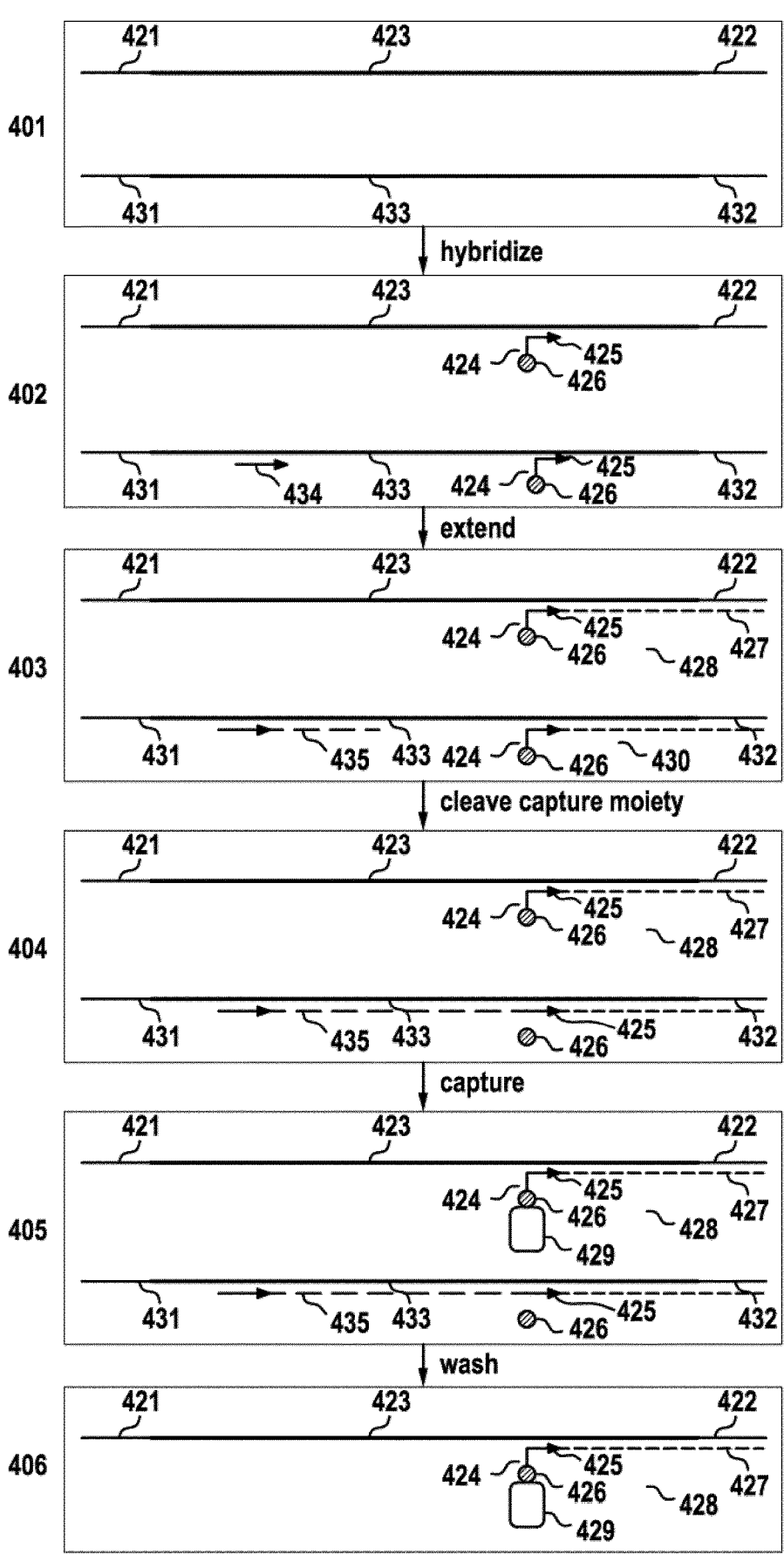
FIG. 4 illustrates a method of primer extension target enrichment where the hybridization to and extension of a poison primer along a non-target nucleic acid molecule cleaves a target capture moiety from a mis-primed target capture primer in accordance with one embodiment of the present disclosure.

The skilled artisan will appreciate that the extension of the poison primer will, in some embodiments, prevent or mitigate a target capture primer from mis-priming to a non-target strand (compared panel 303 of FIG. 3A with panels 402 and 403 of FIG. 4). Said another way, the formation of the double-stranded polynucleic acid prevents or mitigates a target capture primer from binding to the non-target nucleic acid molecule, and thus prevents or mitigates mis-priming.

Next, the target capture primer extension complex 328 is captured onto a functionalized substrate 329 (see, panel 304 of FIG. 3A). In some embodiments functionalized substrate comprises a solution-phase support (e. g., a bead or another like particle), or a solid-phase support (e.g., a silicon wafer, a glass slide, or the like). Examples of magnetic glass particles and devices employing the same are described in U.S. Pat. Nos. 656,568, 6,274,386, 7,371,830, 6,870,047, 6,255,477, 6,746,874 and 6,258,531, the disclosures of which are hereby incorporated by reference herein in their entireties. In the embodiment illustrated in panel 304, the target capture primer extension complex 328 is captured on the functionalized substrate 329 via the capture moiety 326.

In some embodiments, the capture moiety 326 comprises biotin and the functionalized substrate comprises streptavidin. An alternative method of target capture is described further herein (see, e.g., the embodiment of FIG. 5).

Figure 3B:
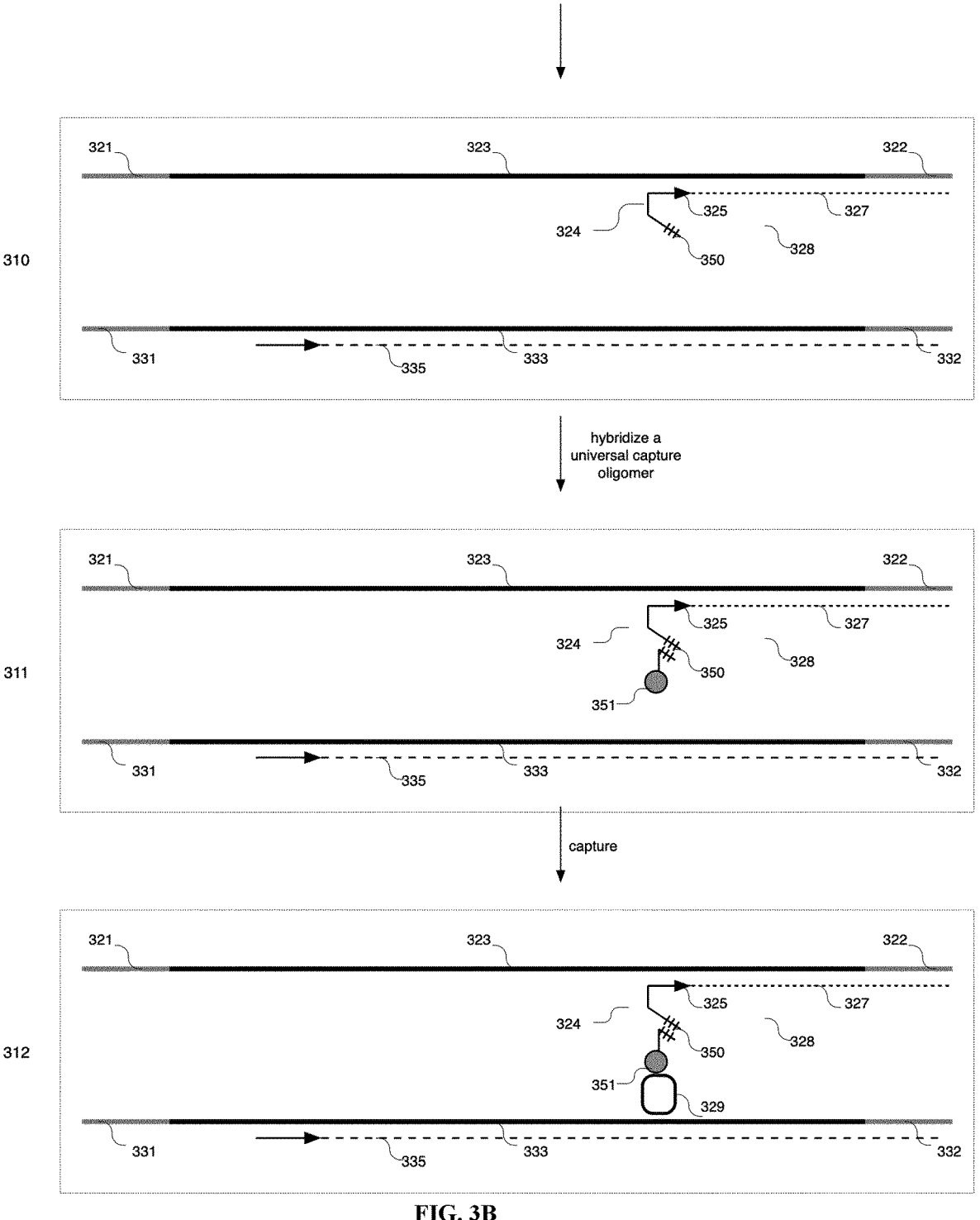
FIG. 3B illustrates an alternative method of target nucleic acid molecule capture utilizing universal capture oligonucleotides.

In some embodiments, and with reference to FIG. 3B, capture comprises hybridizing a universal capture oligonucleotide 351 to the target capture primer 324. In this particular embodiment, the target capture primer 324 comprises a portion which includes a capture sequence, i.e. universal nucleic acid sequence 350 (see panel 310). The introduced universal capture oligonucleotide 351 includes a portion having a nucleic acid sequence that is complementary to the universal capture sequence 350 of the target capture primer 324; and further includes a capture moiety 351. As with the embodiment depicted in panel 304 of FIG. 3A, capture further comprises introducing a functionalized substrate 329, where the functionalized substrate 329 includes a moiety capable of reacting with or binding to the capture moiety 351.

Following capture, the target capture primer extension complex 328 is enriched relative to the nucleic acid molecules present in the nucleic acid library. In some embodiments, enrichment comprises removing the nucleic acid molecules not captured onto the functionalized substrate. In some embodiments, the nucleic acid molecules not captured may be removed by flowing one or more wash and/or buffer solutions through a column including a solution-phase support. By comparing panels 301 and 305, the skilled artisan will appreciate that following capture of the one or more target capture primer extension complexes and the removal of un-captured nucleic acid molecules, the initial reaction mixture becomes enriched with the one or more captured target nucleic acid molecules. In some embodiments, the captured target nucleic acid molecules are directly amplified while coupled to the functionalized surface. In other embodiments, and as described further herein (see FIG. 7), the target capture primer extension complex 328 may be released from the functionalized substrate 329 such that the target nucleic acid molecule may be utilized in further downstream processing operations (e.g. amplification and/or sequencing).

FIG. 4 depicts a method of target nucleic acid enrichment where an extended poison primer prevents the capture of non-target nucleic acid molecules that have been mis-primed with a target capture primer. As described herein, the extension of a poison primer hybridized to a non-target nucleic acid molecule cleaves the capture moiety from a formed target capture primer extension complex. Turning first to panel 401 of FIG. 4, a library of nucleic acid molecules is first prepared, where the library of nucleic acid molecules includes one or more target nucleic acid molecules 423 and one or more non-target nucleic acid molecules 433. In some embodiments, adapters (421, 422, 431, and 432) are ligated to both ends of the one or more target nucleic acid molecules 423 and the one or more non-target nucleic acid molecules 433. In some embodiments, the one or more target nucleic acid molecules 423 are in low abundance as compared with the one or more non-target nucleic acid molecules in the nucleic acid molecule library. For example, in some embodiments the one or more target nucleic acid molecules may represent less than about 10% of the nucleic acid molecules in the nucleic acid molecule library. In other embodiments the one or more target nucleic acid molecules may represent less than about 5% of the nucleic acid molecules in the nucleic acid molecule library. Panel 401 illustrates a target nucleic acid molecule 423, where the target nucleic acid molecule includes a first end comprising a first adapter 401 and a second end comprising a second adapter 422.

Panel 401 further illustrates a non-target nucleic acid molecule 433, where the non-target nucleic acid molecule includes a first end comprising a first adapter 431 and a second end comprising a second adapter 433. The first adapters 421 and 431 are located at the 5' ends of the target and non-target nucleic acid molecules, respectively. The second adapters 422 and 432 are located at the 3' ends of the target and non-target nucleic acid molecules, respectively. In some embodiments, the first adapters 421 and 431 are the same; likewise, in some embodiments the second adapters 431 and 432 are the same.

Following the preparation of the nucleic acid library, one or more target capture primers 424 and one or more poison primers 434 are hybridized to the target and non-target nucleic acid molecules 423 and 433, respectively (see, panel 402 of FIG. 4). In some embodiments, the one or more target capture primers 424 each include a target capture region 425 that is complementary to at least a portion of the target nucleic acid molecule 423 and a capture moiety 426 (e.g., biotin).

Also illustrated in panel 402 of FIG. 4 is the mis-priming of a target capture primer 424 to a non-target nucleic acid molecule sequence 433. Said another way, in some embodiments a target capture primer 424 comprising a capture moiety 426 may hybridize to a non-target nucleic acid molecule 433, i.e., the target capture primer becomes "mis-primed." As such, the non-target nucleic acid molecule may comprise both a hybridized poison primer and a hybridized and mis-primed target capture primer.

In some embodiments, the one or more poison primers 434 include a non-target specific region that is complementary to at least a portion of the non-target nucleic acid molecule 433. Notably, the one or more poison primers 434 do not include a capture moiety, and thus are not capable of being captured in downstream processes.

As illustrated in panel 403 of FIG. 4, each of the one or more hybridized target capture primers, including those that have been mis-primed, and the one or more poison primers are extended. In some embodiments, the one or more target capture primers 424 hybridized to the target nucleic acid molecule are extended with a first polymerase (not shown), thereby producing one or more target capture primer extension complexes 428. The one or more target capture primer extension complexes 428 each include a target nucleic acid molecule 423 and an extended target capture primer 427 (with the dashed line indicating the extended portion of the hybridized target capture primer 424). In some embodiments, the target capture primer hybridized to the non-target nucleic acid molecule is also extended by a first polymerase (not shown), thereby producing one or more mis-primed extension complexes 430. As further illustrated in panel 403, the one or more hybridized poison primers 434 are extended with a second polymerase (not shown), thereby producing one or more extended poison primers 435 (where the dashed line again indicates the extended portion of the hybridized poison primer 434).

As further illustrated in panel 404 of FIG. 4, as the poison primer continues to be extended, the extended poison primer clips the capture moiety 426 from the target capture primer, thus releasing the capture moiety from the target capture primer extension complex. The skilled artisan will appreciate, that by virtue of the extension of the hybridized poison primer, the incidence of the capture of a non-target nucleic acid molecule is prevented or reduced.

Next, the target capture primer extension complex 428 is captured with a functionalized substrate 429 (see panel 405 of FIG. 4). In some embodiments functionalized substrate is a solution-phase support (e. g., a bead or another like particle), or a solid-phase support (e.g., a silicon wafer, a glass slide, or the like). As noted above, any of the magnetic glass particles and devices employing the same as described in U.S. Pat. Nos. 656,568, 6,274,386, 7,371,830, 6,870,047, 6,255,477, 6,746,874 and 6,258,531 may be utilized. In the embodiment illustrated in panel 405, the target capture primer extension complex 428 is captured on the functionalized substrate 429 via the capture moiety 426. An alternative method of target capture is described herein (see, e.g., the embodiment of FIG. 6).

Following capture, the target capture primer extension complex 428 is enriched relative to the nucleic acid molecules present in the nucleic acid library. In some embodiments, enrichment comprises removing the nucleic acid molecules not captured onto the functionalized substrate, e.g. the nucleic acid molecules not captured may be removed by flowing one or more wash and/or buffer solutions through a column including a solution-phase support. By comparing panels 401 and 406, the skilled artisan will appreciate that following capture of the one or more target capture primer extension complexes and the removal of un-captured nucleic acid molecules, the initial reaction mixture becomes enriched with the one or more captured target nucleic acid molecules. In some embodiments, the captured target nucleic acid molecules are directly amplified while coupled to the functionalized surface. In other embodiments, and as described further herein (see FIG. 7), the target capture primer extension complex 428 may be released from the functionalized substrate 429 such that the target nucleic acid molecule may be utilized in further downstream processing operations (e.g., amplification and/or sequencing).

Figure 5:
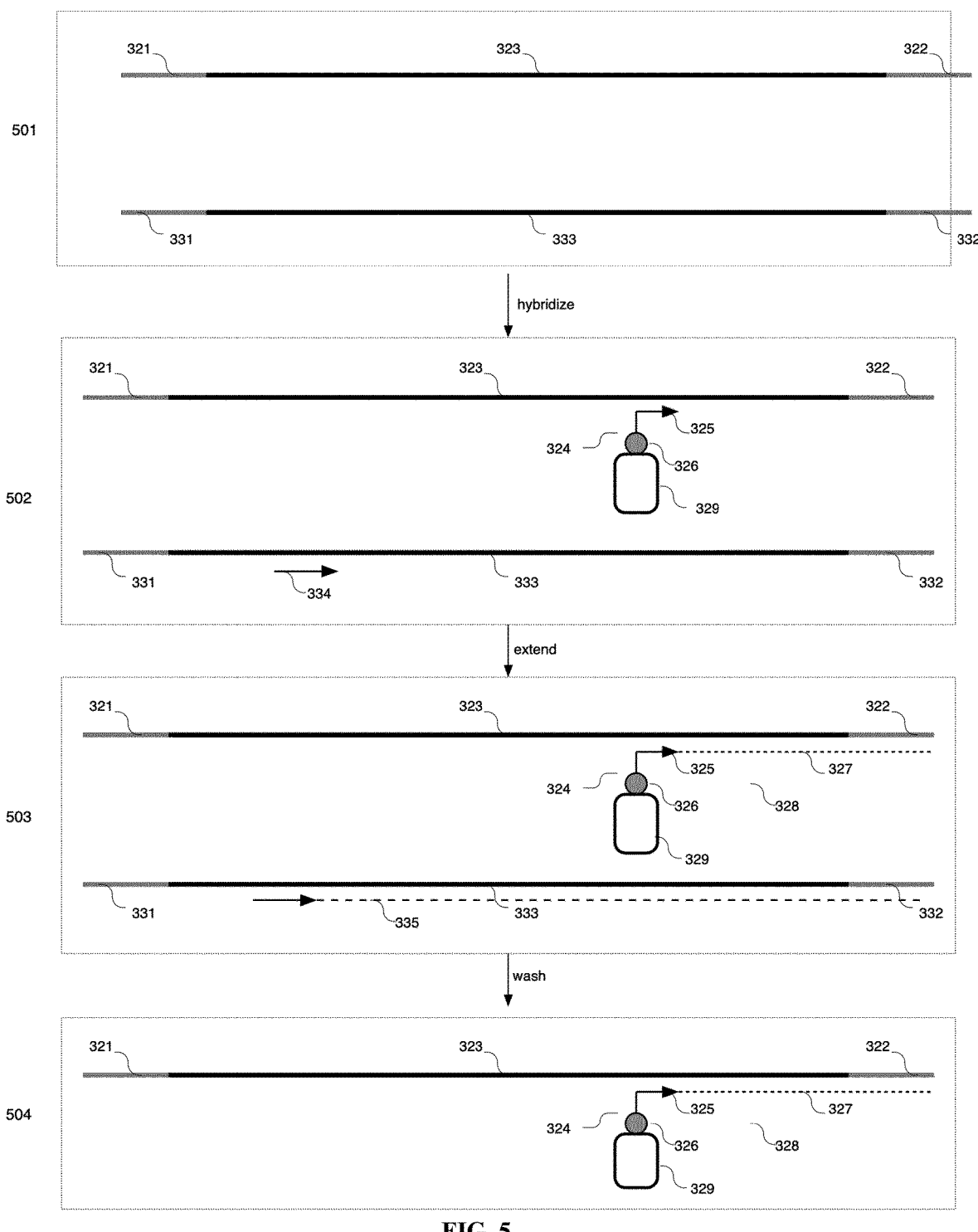
FIG. 5 illustrates an alternative embodiment to that depicted in FIG. 3A, where the target capture primer is coupled to a substrate through a capture moiety prior to its hybridization to a target nucleic acid molecule in accordance with one embodiment of the present disclosure.

As noted herein, a capture moiety of a target capture primer may be bound to a functionalized substrate prior to hybridization of the target capture primer to the target nucleic acid molecule. FIG. 5 depicts an alternative workflow where a target capture primer 324 is bound to a functionalized substrate 329 through the capture moiety 326 prior to its hybridization to the target nucleic acid molecule 323. In some embodiments, the target capture primer 324 bound to the functionalized substrate 329 is hybridized to the target nucleic acid molecule 323 (see panel 502). Contemporaneously, a poison primer 334 is hybridized to the non-target nucleic acid molecule 333 (see panel 502). As with the embodiment depicted in FIG. 3A, both the hybridized target capture primer 324 and the hybridized poison primer 334 are extended. In some embodiments, the extension of the poison primer prevents or reduces mis-priming of target capture primers to the non-target nucleic acid molecule 333. As shown in panel 503, the target capture primer extension complex 328 is bound to the functionalized substrate 329 through the capture moiety 326, and thus is no separate capture step is required (compare to panel 304 of FIG. 3A). In some embodiments, enrichment comprises removing the nucleic acid molecules not captured onto the functionalized substrate, e.g. the nucleic acid molecules not captured may be removed by flowing one or more wash and/or buffer solutions through a column including a solution-phase support. As described further herein, the target capture primer extension complex 328 may be released from the functionalized substrate 329 such that the target nucleic acid molecule may be utilized in further downstream processing operations (e.g., sequencing).

Figure 6:
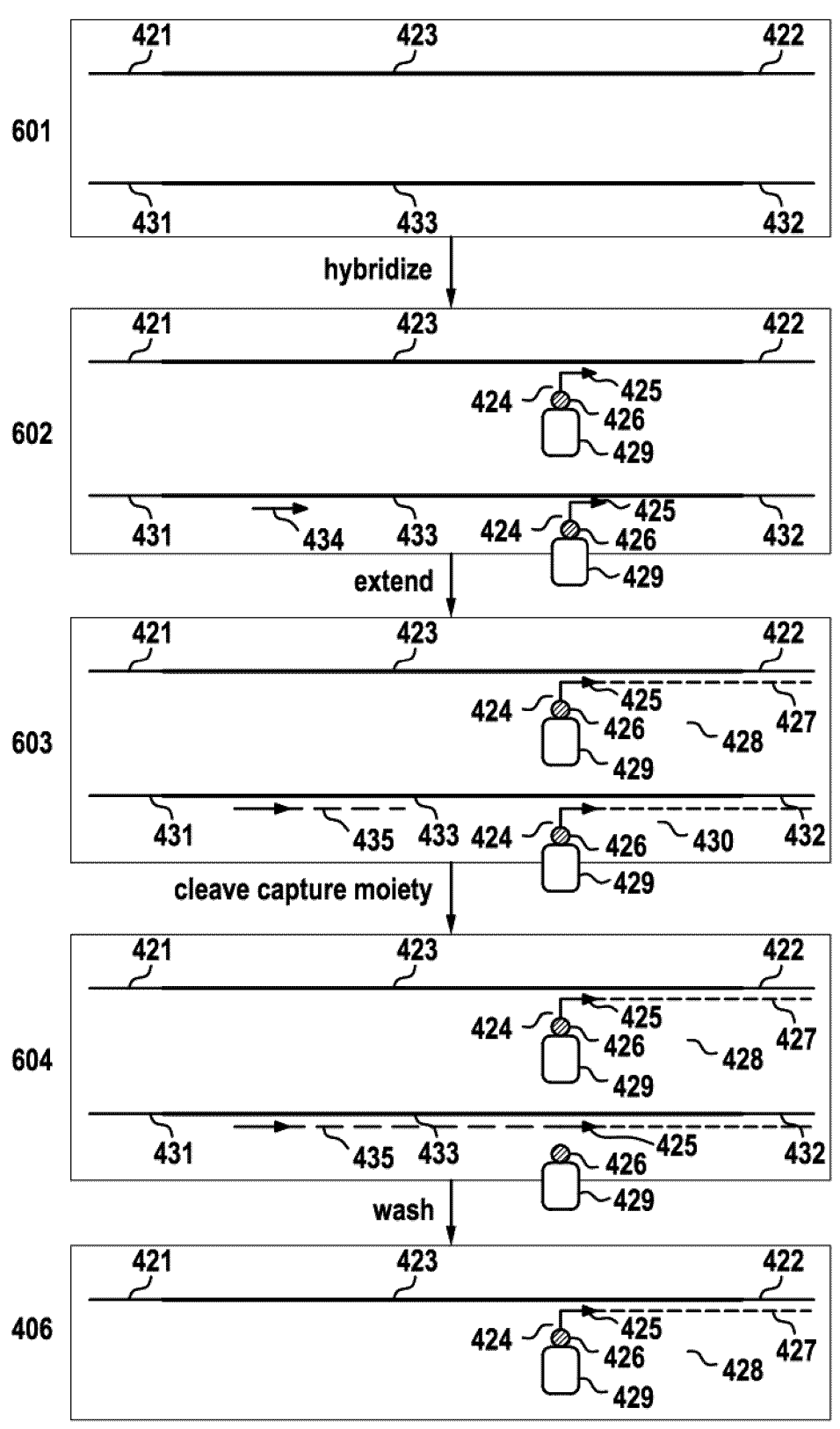
FIG. 6 illustrates an alternative embodiment to that depicted in FIG. 4, where the target capture primer is coupled to a substrate through a capture moiety prior to its hybridization to a target nucleic acid molecule in accordance with one embodiment of the present disclosure.

FIG. 6 depicts another alternative workflow where a target capture primer 424 is bound to a functionalized substrate 429 through the capture moiety 426 prior to its hybridization to the target nucleic acid molecule 423. In some embodiments, the target capture primer 424 bound to the functionalized substrate 429 is hybridized to the target nucleic acid molecule 423 (see panel 602). Contemporaneously, a poison primer 434 is hybridized to the non-target nucleic acid molecule 433 (see panel 502). Also shown in panel 602 is the mis-priming of a target capture primer 424 (also bound to a functionalized substrate 429 through the capture moiety 426) to the non-target nucleic acid molecule 433. As with the embodiment depicted in FIG. 4, both the hybridized target capture primer 424 and the hybridized poison primer 434 are extended (see panel 603). As depicted in panel 604 of FIG. 6, as the poison primer 434 continues to be extended, the extended poison primer clips the capture moiety 426 and bound functionalized substrate 429 from the target capture primer, thus releasing the capture moiety from the target capture primer extension complex 428.

As shown in panel 604, the target capture primer extension complex 428 is bound to the functionalized substrate 429 through the capture moiety 426, and thus is no separate capture step is required (compare to panel 405 of FIG. 4). In some embodiments, enrichment comprises removing the nucleic acid molecules not captured onto the functionalized substrate, e.g., the nucleic acid molecules not captured may be removed by flowing one or more wash and/or buffer solutions through a column including a solution-phase support. As described further herein, the target capture primer extension complex 428 may be released from the functionalized substrate 429 such that the target nucleic acid molecule may be utilized in further downstream processing operations (e.g., sequencing).

Figure 7:
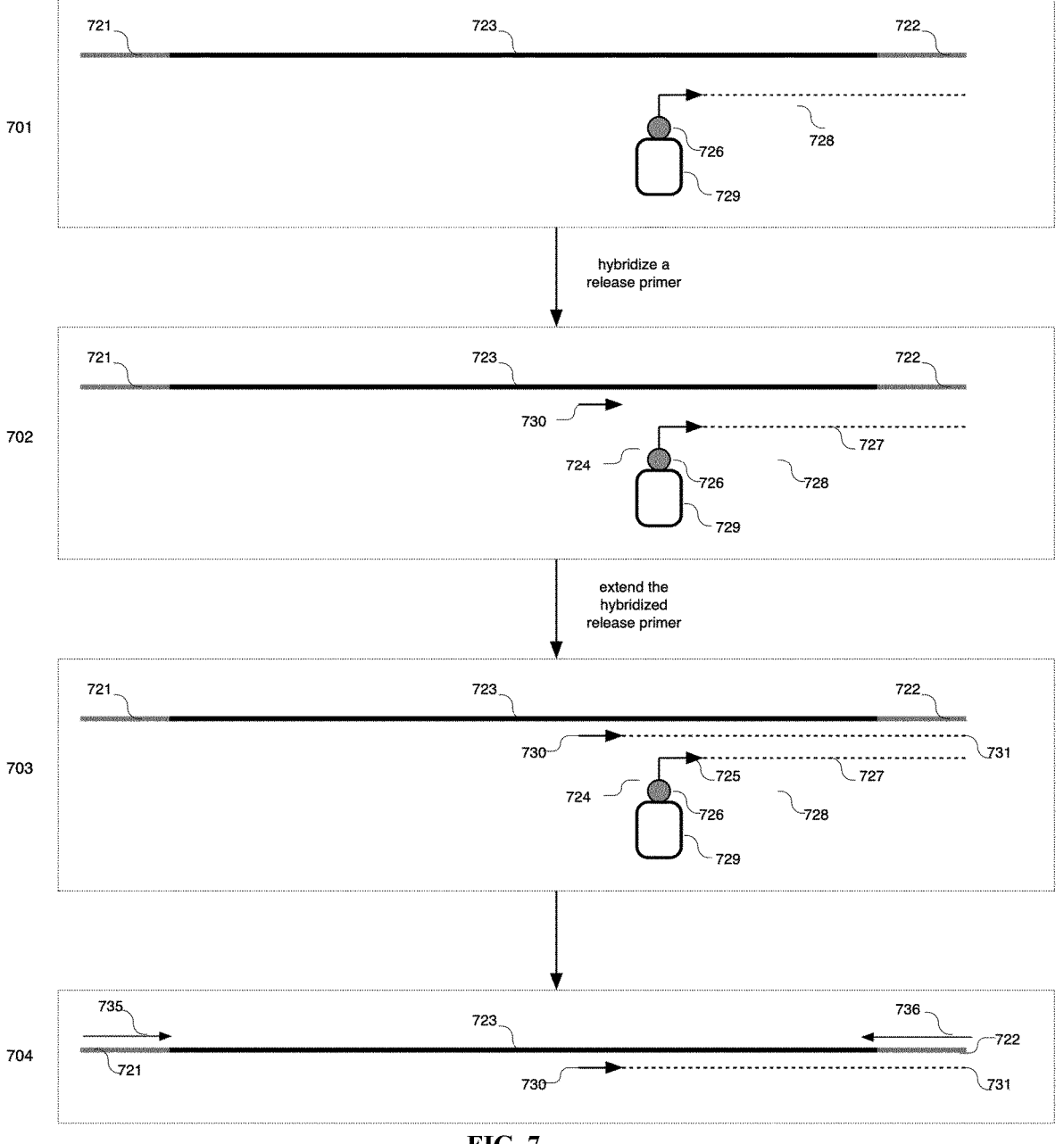
FIG. 7 sets forth a method of releasing an extended hybridized target capture primer from a target nucleic acid molecule prior to amplification and/or sequencing of the target nucleic acid molecule in accordance with one embodiment of the present disclosure.

As noted above, in some embodiments, a target capture primer extension complex may be released from a functionalized substrate such that a target nucleic acid molecule may be amplified and/or sequenced. FIG. 7 depicts a target capture prime extension complex 728 coupled to a functionalized substrate 729 through a capture moiety 726 (see panel 701 of FIG. 7). In some embodiments, a release primer 730 is hybridized to the target nucleic acid molecule 723 (see panel 702). In some embodiments, the release primer 730 is complementary to the target nucleic acid molecule 723 and hybridizes to the target nucleic acid molecule 723 at a 5' position relative to the target capture primer extension complex 728. As depicted in panel 702, both the target capture primer extension complex 728 (which is attached to the functionalized substrate 729) and the release primer 730 are hybridized to the target nucleic acid molecule 723.

With reference to panel 703 of FIG. 7, the hybridized release primer 730 is extended with a third polymerase (not shown), thereby providing an extended release primer 731. In some embodiments, the extension of the hybridized release primer 730 liberates the extended target capture primer 727 from the target capture primer extension complex 728. In some embodiments, the extended target capture primer 727 remains attached to the solid support 218.

As illustrated in FIG. 2E, the target nucleic acid molecule 723 is amplified with a fourth polymerase (not shown), a first amplification primer 735, and a second amplification primer 736. The first amplification primer 735 includes a 3' end complementary to the first adapter 721 and the second amplification primer 736 includes a 3' end complementary to the second adapter 722. In some embodiments, the first and second amplification primers are universal primers.

Example

Figure 8:
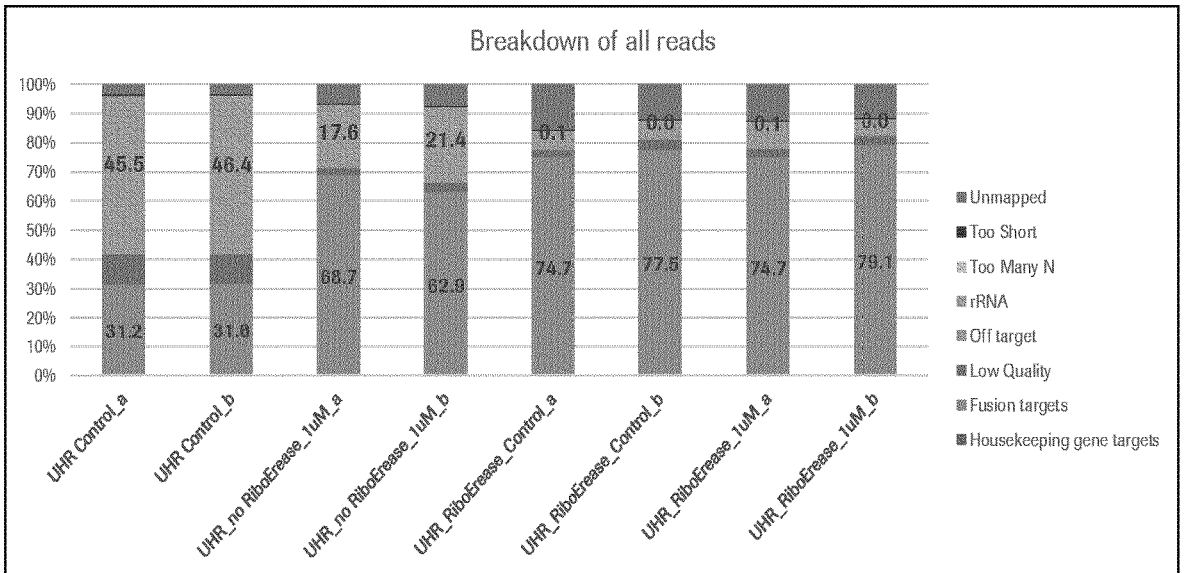
FIG. 8 depicts the results of an experiment where sgPETE showed an average of ~45% rRNA reads in sequencing reads using 10 ng UHR RNA as input into library preparation and capture. The average number of rRNA reads was ~25% lower when 1 μM poison primers was included in the sgPETE capture reaction. In ribo-depleted samples the inclusion of poison primer did not result in a significant increase in off-target reads.
Figure 9A:
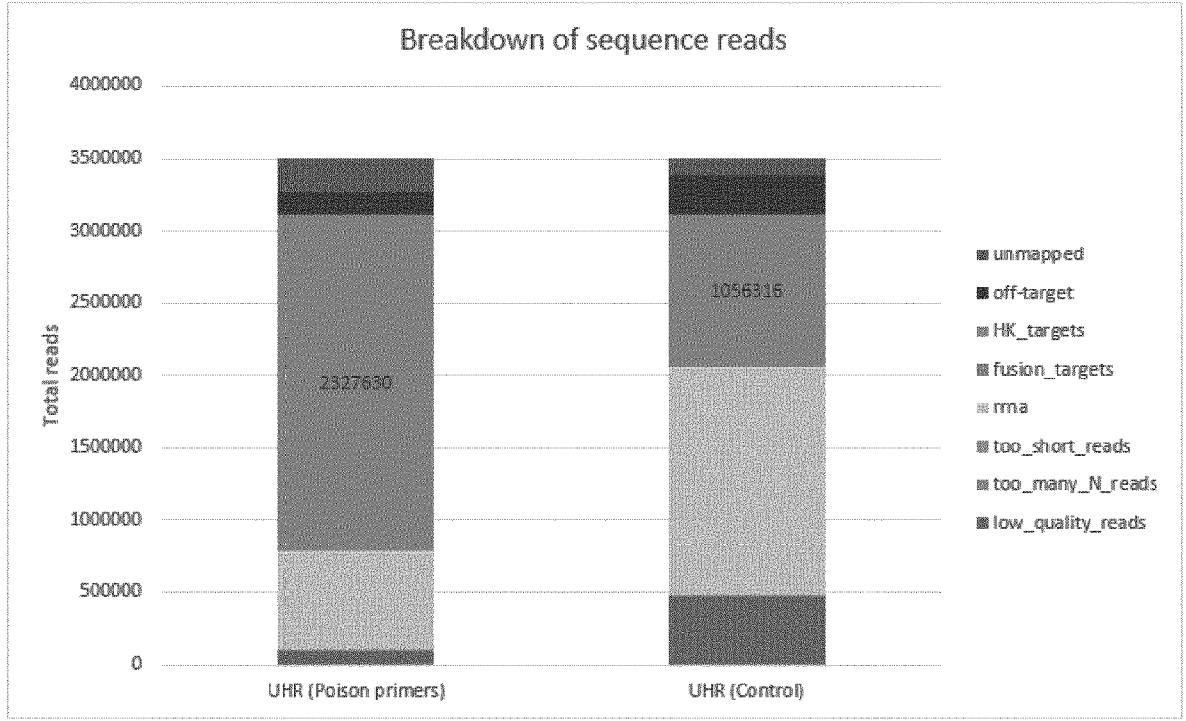
FIG. 9A depicts breakdown of sequencing reads sub-sampled to 3.5 million. With poison primers included 2.33 million (±0.17 million) fusion target reads and 1.05 million (±0.08 million) fusion reads in the control samples.
Figure 9B:
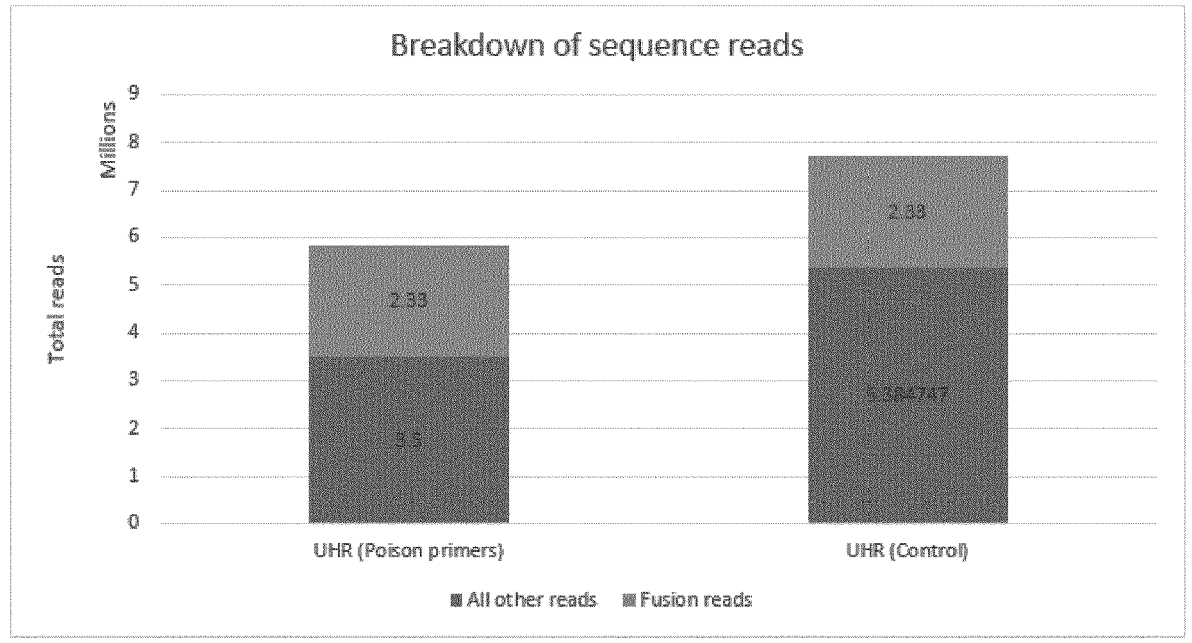
FIG. 9B illustrates a theoretical sequencing depth and breakdown of reads required for control samples the detect similar number of fusion targets.

Proof of principal was performed using universal human reference UHR (Agilent) RNA as test material with a 25 ng input mass. cDNA libraries were prepared using Kapa RNA HyperPrep. rRNA depleted libraries were prepared as positive controls, using Kapa Ribo-Erase. Poison primers were designed against both strands of human rRNA derived cDNA using the reference GRCh38. The rRNA poison primers consisted of 98 primers (SEQ ID NOS: 1-98) designed with a $T_m$ between 54° C. and 58° C. The NCBI nucleotide archive (https://www.ncbi.nlm.nih.gov/nuccore) was searched with the query "*Homo sapiens*" [Organism] AND "ribosomal rna" [All Fields] AND biomol_rrna [PROP]" to identify all human rRNA genes. The nucleotide sequences were aligned using clustalW to investigate sequence similarity. Based on sequence similarities, the list was reduced to representative rRNAs (Table 1). All possible putative primers of length 16-31 bp was created for listed rRNA sequences. The primer sequences were aligned to the human reference genome GRCh38 using blat (https://github.com/dib-lab/ged-docs/wiki/BLAT). Putative primers were filtered for favorable PCR amplification properties based on number of mapping positions and thermal melting point (>54° C.). Primers were selected to span each rRNA target on both positive and negative strand with little to no overlap between primers. Poison primers were included in the capture reaction with the capture primers. Target capture primers consisted of 152 primers which were designed to detect known gene fusions with a mean $T_m$ of 55° C. The target capture primers were accompanied by 152 primers designed to release captured fragments from streptavidin in a subsequent release reaction (the "release primers"). The input into capture extension included reactions with poison primers at 1 μM and without poison primers as control. The capture extension reactions included: 1 μg cDNA, Kapa 2G multiplex mix (5×), 10 μL Blocking Oligo (37.3 μM), 2 μL Capture Primer Pool (1.64 nM/primer) and 2 μL, poison primer pool (5 nM/primer), and 16 μL ddH2O. The capture extension reaction was performed using the following thermal cycling: 95° C. for 2 min, 80° C. for 1 sec, 2% ramp to 60° C. for 10 min, 65° C. for 2 min and hold at 4° C. The extension product was captured by incubating with streptavidin magnetic beads in 1× binding buffer (100 mM NaCl, 10 mM Tris-HCl, 2% SDS). Beads were washed using washing buffer. Release primers were hybridized to beads captured targets at 55° C. for 30 min. Release primer extension was performed using sgPETE release mix at 50° C. for 2 min. Final release reaction was amplified using Kapa HiFi ReadyMix using 15 amplification cycles. The success of poison primer depletion was assessed by sequencing on the Illumina Nextseq 500 using a 2×150 bp reads workflow. The number of demultiplexed reads for each sample ranged from 3.98 million to 10.1 million. For bioinformatics analysis the number of reads used for all samples were subsampled to 3.5 million reads. The quality filtered sequencing reads filtered using fastp were deduplicated using UMI tools using default settings. The sequencing reads that map to rRNA reads were mapped using BWM MEM. The remaining non-rRNA reads were mapped to the RNA reverence Hg38 using STAR aligner. With reference to FIG. 8, the UHR control sample had cDNA without rRNA depletion as input, with no poison primers added into the capture reaction. The UHR no RiboErase 1 μM samples had cDNA without rRNA depletion as input and contained 1 μM poison primers in the capture reaction. The samples containing poison primers showed a decrease in the abundance of off target rRNA fragments being sequenced with a mean of 19.47% (±4.17%) compared to the control samples with a mean of 44.83% (±1.97%). The number of desired targets also increased when poison primers are included in the capture reaction. With the 3.5 million reads subsample, 2.33 million (±0.17 million) fusion target reads were detected when poison primers were included and 1.05 million (±0.08 million) sequencing reads in the control samples (FIG. 9A). The inclusion of poison primers thus resulted in a higher read depth for the fusion targets with the same overall sequencing depth. In the example the control sample will require a theoretical 7.71 million reads to reach the same reads depth for the fusion target as the poison primer treatment (FIG. 9B). The % reads off-target and unmapped reads did not differ significantly between Ribo-Erase treated samples and Ribo-Erase treated samples that included poison primers. Thus including poison primer had no negative effect on the sequencing metrics as observed for the Ribo-Erase treated samples (FIG. 8).

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

---

The invention claimed is:

1. A method of enriching at least one target nucleic acid molecule in a library of nucleic acid molecules, wherein the at least one target nucleic acid molecule originates from genomic nucleic acid molecules, wherein the method comprises the following steps:
   (a) hybridizing a first target capture primer to a first target nucleic acid molecule in the library of nucleic acid molecules, wherein the first target capture primer comprises a capture moiety;
   (b) hybridizing a first poison primer to a first non-target nucleic acid molecule in the library of nucleic acid molecules, wherein the first non-target nucleic acid molecule is ribosomal RNA (rRNA), wherein the first poison primer does not include any capture moiety;
   (c) extending both the first hybridized target capture primer and the first hybridized poison primer, wherein the extension of the first hybridized target capture primer provides a first target capture primer extension complex comprising the first target nucleic acid molecule and the extended first target capture primer,
   wherein (i) the extension of the first hybridized poison primer prevents the first target capture primer from hybridizing to the first non-target nucleic acid molecule, or (ii) the extension of the first hybridized poison primer displaces a first target primer hybridized to the first non-target nucleic acid molecule; and
   (d) enriching the first target nucleic acid molecule relative to the library of nucleic acid molecules in the library of nucleic acid molecules.

2. The method of claim 1, wherein the first target capture primer and the first poison primer are added as a pool of primers to the library of nucleic acid molecules.

3. The method of claim 1, wherein each of the nucleic acid molecules in the library of nucleic acid molecules comprises a first end including a first adapter and a second end including a second adapter.

4. The method of claim 3, further comprising the step of amplifying the first target nucleic acid molecule with a first amplification primer and a second amplification primer, wherein the first amplification primer comprises a 3' end complementary to the first adapter, and wherein the second amplification primer comprises a 3' end complementary to the second adapter.

5. The method of claim 4, further comprising the step of sequencing the amplified target nucleic acid molecule.

6. The method of claim 1, wherein the enriching of the first target nucleic acid molecule relative to the library of nucleic acid molecules comprises: (i) capturing the first target capture primer extension complex; (i) removing uncaptured non-target nucleic acid molecules; and (ii) releasing the first target nucleic acid molecule from the captured first target capture primer extension complex.

7. The method of claim 6, wherein the capturing of the first target capture primer extension complex comprises: contacting the first target capture primer extension complex with a functionalized substrate.

8. The method of claim 7, wherein the capture moiety of the first target capture primer comprises a first member of a pair of specific binding entities, and wherein the functionalized substrate comprises a second member of the pair of specific binding entities.

9. The method of claim 8, wherein the first member of the pair of specific binding entities is selected from the group consisting of biotin, an antigenic molecule, an enzyme substrate, a receptor ligand, a polysaccharide, a thiolated molecule, and an amine-terminated molecule.

10. The method of claim 8, wherein the second member of the pair of specific binding entities is selected from the group consisting of streptavidin, an antibody, an enzyme, a receptor, a lectin, a gold particle, and an NHS-activated moiety.

11. The method of claim 7, wherein the first target capture primer is coupled to a substrate through the capture moiety prior to the hybridizing of the first target capture primer to the first target nucleic acid molecule in the library of nucleic acid molecules, and wherein the hybridizing of the first target capture primer to the first target nucleic acid molecule and the extending of the first hybridized target capture primer thereby captures the first target nucleic acid molecule to the substrate.

12. The method of claim 6, wherein the capturing of the first target capture primer extension complex comprises: (i) hybridizing a universal capture oligonucleotide to the capture moiety of the first target capture primer extension complex to form a universal capture oligonucleotide complex, wherein the universal capture oligonucleotide comprises (1) a first member of a pair of specific binding entities, and (2) a nucleotide sequence complementary to at least a portion of a capture sequence of the capture moiety; (ii) contacting the universal capture complex with a functionalized substrate, wherein the functionalized substrate comprises a second member of the pair of specific binding entities.

13. The method of claim 6, wherein the removing of the un-captured nucleic acid molecules comprises washing away the un-captured non-target nucleic acid molecules.

14. The method of claim 6, wherein the releasing of the captured first target capture primer extension complex comprises: (i) hybridizing a release primer to the first target nucleic acid molecule; and (ii) extending the hybridized release primer.

15. The method of claim 14, wherein the hybridized first target capture primer is extended with a first polymerase, and wherein the hybridized release primer is extended with a second polymerase.

16. The method of claim 15, wherein the first and second polymerases are different.

17. The method of claim 1, wherein the first target capture primer has a melting temperature which is greater than a melting temperature of the first poison primer.

18. The method of claim 1, wherein the library of nucleic acid molecules comprises a plurality of target nucleic acid molecules and a plurality of non-target nucleic acid molecules, wherein the plurality of target nucleic acid molecules are in low abundance as compared with the plurality of non-target nucleic acid molecules.

19. The method of claim 18, wherein the plurality of target nucleic acid molecules comprise less than about 10% of the nucleic acid molecules in the library of nucleic acid molecules.

20. The method of claim 18, wherein the plurality of target nucleic acid molecules comprise less than about 5% of the nucleic acid molecules in the library of nucleic acid molecules.

21. The method of claim 18, wherein the plurality of target nucleic acid molecules comprise fusion transcripts.

\* \* \* \* \*

SEQUENCE LISTING

```
<160> NUMBER OF SEQ ID NOS: 98

<210> SEQ ID NO 1
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 1
gatccaccgc taagagtc                                                  18

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 2
cattaattct cgcagctagc                                                20

<210> SEQ ID NO 3
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 3
tgtctgagcg tcgctt                                                    16

<210> SEQ ID NO 4
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 4
```
gtggtatggc cgtagac                                                          17

<210> SEQ ID NO 5
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 5
gggtgctgta ggcttt                                                           16

<210> SEQ ID NO 6
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 6
ggcaggatca accaggta                                                         18

<210> SEQ ID NO 7
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 7
cactgtaccg gccgtg                                                           16

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 8
ataactgtgg taattctaga gcta                                                  24

<210> SEQ ID NO 9
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 9
aaatgcacgc atcccc                                                           16

<210> SEQ ID NO 10
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 10

-continued

```
taacctcggg ccgatc                                        16

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 11
gcgactacca tcgaaagt                                      18

<210> SEQ ID NO 12
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 12
ggggaggtag tgacgaa                                       17

<210> SEQ ID NO 13
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 13
caattacagg gcctcgaa                                      18

<210> SEQ ID NO 14
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 14
gatcttggga gcgggc                                        16

<210> SEQ ID NO 15
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 15
aagagcatcg aggggg                                        16

<210> SEQ ID NO 16
<211> LENGTH: 22
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 16
ctattttgtt ggttttcgga ac                                 22
```

```
<210> SEQ ID NO 17
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 17
cgccggtcca agaattt                                               17

<210> SEQ ID NO 18
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 18
ataaacgatg ccgaccg                                               17

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 19
ccggaaccca aagacttt                                              18

<210> SEQ ID NO 20
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 20
ggacacggac aggattg                                               17

<210> SEQ ID NO 21
<211> LENGTH: 23
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 21
aaagagctat caatctgtca atc                                        23

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 22
tgctaactag ttacgcgac                                             19
```

-continued

```
<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 23
catcacagac ctgttattgc                                              20

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 24
ttgcaattat tccccatgaa c                                            21

<210> SEQ ID NO 25
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 25
gcacttactg ggaattcct                                               19

<210> SEQ ID NO 26
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 26
gagcgctgag aagacg                                                  16

<210> SEQ ID NO 27
<211> LENGTH: 25
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 27
cttttacttc ctctagatag tcaag                                        25

<210> SEQ ID NO 28
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 28
ctgatctgag gtcgcg                                                  16
```

-continued

```
<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 29
gggaatcctg gttagtttct t                                                    21

<210> SEQ ID NO 30
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 30
gcccaagtcc ttctgatc                                                        18

<210> SEQ ID NO 31
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 31
ccaagcaacc cgactc                                                          16

<210> SEQ ID NO 32
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 32
taaacgggtg gggtcc                                                          16

<210> SEQ ID NO 33
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 33
gccgggttga atcctc                                                          16

<210> SEQ ID NO 34
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 34
cctcctcctc ctcccc                                                          16

<210> SEQ ID NO 35
```

```
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 35 gggggctgt aacact                                                    16

<210> SEQ ID NO 36
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 36
gtgggtagcc gacgtc                                                   16

<210> SEQ ID NO 37
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 37
tctccagtcc gccgag                                                   16

<210> SEQ ID NO 38
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 38
ctcgtgctcc acctcc                                                   16

<210> SEQ ID NO 39
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 39
cgtccgacct gggtata                                                  17

<210> SEQ ID NO 40
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 40
cagctatcct gagggaaac                                                19

<210> SEQ ID NO 41
<211> LENGTH: 17
```

```
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 41
ggaatgcgag tgcctag                                               17

<210> SEQ ID NO 42
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 42
ccttaacccg gcgttc                                               16

<210> SEQ ID NO 43
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 43
cacctgccga atcaact                                              17

<210> SEQ ID NO 44
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 44
gctcccgtcc actctc                                              16

<210> SEQ ID NO 45
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 45
ctcctactcg tcgcgg                                              16

<210> SEQ ID NO 46
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 46
gagaagggtt ccatgtgaa                                           19

<210> SEQ ID NO 47
<211> LENGTH: 17
<212> TYPE: DNA
```

-continued

```
<213> ORGANISM: Artificial Sequence
<220> FEATURE:
<221> NAME/KEY: source
<223> OTHER INFORMATION: /note="Synthetic poison primer"

<400> SEQUENCE: 47
ccgactgacc catgttc                                                         17

<210> SEQ ID NO 48
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 48
ggattcgggg atctgaac                                                        18

<210> SEQ ID NO 49
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 49
gttcgccccg agagag                                                          16

<210> SEQ ID NO 50
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 50
gacgctttcc aaggca                                                          16

<210> SEQ ID NO 51
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 51
ccaaggtgaa cagcctc                                                         17

<210> SEQ ID NO 52
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 52
ggcttgccga cttccc                                                          16

<210> SEQ ID NO 53
<211> LENGTH: 16
<212> TYPE: DNA
<213> ORGANISM: Artificial Sequence
```

```
<220> FEATURE:
<221> NAME/KEY: source
<223> OTHER INFORMATION: /note="Synthetic poison primer"

<400> SEQUENCE: 53
ctcgcgtcca gagtcg                                          16

<210> SEQ ID NO 54
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 54
taagtcggct gctaggc                                         17

<210> SEQ ID NO 55
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 55
gcgggagtaa ctatgactc                                       19

<210> SEQ ID NO 56
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 56
catgcgcgtc actaattag                                       19

<210> SEQ ID NO 57
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 57
gaataagtgg gaggccc                                         17

<210> SEQ ID NO 58
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 58
accgggtcag tgaaaaaa                                        18

<210> SEQ ID NO 59
<211> LENGTH: 20
<212> TYPE: DNA
<213> ORGANISM: Artificial Sequence
<220> FEATURE:
```

-continued

```
<221> NAME/KEY: source
<223> OTHER INFORMATION: /note="Synthetic poison primer"

<400> SEQUENCE: 59
tacacctgtc aaacggtaac                                          20

<210> SEQ ID NO 60
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 60
ttctgtcctc cctgagc                                             17

<210> SEQ ID NO 61
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 61
ccaagcgttc atagcga                                             17

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 62
tcacaatgat aggaagagcc                                          20

<210> SEQ ID NO 63
<211> LENGTH: 22
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 63
gttttaccct actgatgatg tg                                       22

<210> SEQ ID NO 64
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 64
ctcagccaag cacataca                                            18

<210> SEQ ID NO 65
<211> LENGTH: 16
<212> TYPE: DNA
<213> ORGANISM: Artificial Sequence
<220> FEATURE:
<221> NAME/KEY: source
```

-continued

<223> OTHER INFORMATION: /note="Synthetic poison primer"

<400> SEQUENCE: 65
gttggcctcg gatagc                                                                16

<210> SEQ ID NO 66
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 66
gttccccacg aacgtg                                                                16

<210> SEQ ID NO 67
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 67
tcgacacaag ggtttgtc                                                              18

<210> SEQ ID NO 68
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 68
aggctaggac caaacctat                                                             19

<210> SEQ ID NO 69
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 69
cagctcaaaa cgcttagc                                                              18

<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 70
aaggttaatc actgctgttt c                                                          21

<210> SEQ ID NO 71
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

-continued

<400> SEQUENCE: 71
atagaagccg gcgtaaag                                                          18

<210> SEQ ID NO 72
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 72
ttattgggga gggggtg                                                           17

<210> SEQ ID NO 73
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 73
gcttagccct aaacctcaa                                                         19

<210> SEQ ID NO 74
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 74
ggctcgtagt gttctgg                                                           17

<210> SEQ ID NO 75
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 75
atataccgcc atcttcagc                                                         19

<210> SEQ ID NO 76
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 76
tgtagccttc atcagggt                                                          18

<210> SEQ ID NO 77
<211> LENGTH: 22
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 77
gaaaactacg atagcccta tg                                                 22

<210> SEQ ID NO 78
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 78
gtgtgtacgc gcttca                                                       16

<210> SEQ ID NO 79
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 79
agtgcacttg gacgaac                                                      17

<210> SEQ ID NO 80
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 80
ggtttggggc taggtttag                                                    19

<210> SEQ ID NO 81
<211> LENGTH: 22
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 81
gcaatagata tagtaccgca ag                                                22

<210> SEQ ID NO 82
<211> LENGTH: 27
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 82
cttgctatat tatgcttggt tataatt                                           27

<210> SEQ ID NO 83
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 83

-continued

```
ctaaaagagc acacccgt                                                    18

<210> SEQ ID NO 84
<211> LENGTH: 19
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 84
cttggacaac cagctatca                                                   19

<210> SEQ ID NO 85
<211> LENGTH: 23
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 85
ctaggaaaaa accttgtaga gag                                              23

<210> SEQ ID NO 86
<211> LENGTH: 18
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 86
tgagcttgaa cgctttct                                                    18

<210> SEQ ID NO 87
<211> LENGTH: 28
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 87
aatgttagta taagtaacat gaaaacat                                        28

<210> SEQ ID NO 88
<211> LENGTH: 20
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 88
ttaatctgac gcaggcttat                                                  20

<210> SEQ ID NO 89
<211> LENGTH: 26
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 89
```
gaaaggttaa aaaaagtaaa aggaac                                                      26

<210> SEQ ID NO 90
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 90
aacaggcggg gtaagat                                                                17

<210> SEQ ID NO 91
<211> LENGTH: 23
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 91
gttcagctgt ctcttacttt taa                                                         23

<210> SEQ ID NO 92
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 92
tgttatgccc gcctct                                                                 16

<210> SEQ ID NO 93
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 93
gagcagaacc caacctc                                                                17

<210> SEQ ID NO 94
<211> LENGTH: 17
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 94
tgtactgctc ggaggtt                                                                17

<210> SEQ ID NO 95
<211> LENGTH: 20
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 95
acaatagggt ttacgacctc                                                             20

-continued

```
<210> SEQ ID NO 96
<211> LENGTH: 16
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 96
ctgcaccatc gggatg                                               16

<210> SEQ ID NO 97
<211> LENGTH: 23
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 97
gtacgaaagg acaagagaaa taa                                       23

<210> SEQ ID NO 98
<211> LENGTH: 25
<212> TYPE: DNA
<213> ORGANISM: Artificial Sequence
<220> FEATURE:
<221> NAME/KEY: source
<223> OTHER INFORMATION: /note="Synthetic poison primer"

<400> SEQUENCE: 98
gtgggtataa tactaagttg agatg                                     25
```